US010035773B2

(12) United States Patent
Pazenok et al.

(10) Patent No.: US 10,035,773 B2
(45) Date of Patent: *Jul. 31, 2018

(54) METHOD FOR PRODUCING 3,5-BIS(FLUOROALKYL)-PYRAZOL-4-CARBOXYLIC ACID DERIVATIVES AND 3,5-BIS(FLUOROALKYL)-PYRAZOLES

(71) Applicants: BAYER CROPSCIENCE AG, Monheim (DE); CENTRE NATIONAL DE LA RECHERCHE SCIENTIFIQUE, Paris (FR)

(72) Inventors: Sergii Pazenok, Solingen (DE); Norbert Lui, Odenthal (DE); Jean-Pierre Vors, Sainte Foy les Lyon (FR); Frederic R Leroux, Herrlisheim (FR); Florence Giornal, Caderousse (FR)

(73) Assignees: BAYER CROPSCIENCE AG, Monheim (DE); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/059,759

(22) Filed: Mar. 3, 2016

(65) Prior Publication Data
US 2016/0185731 A1 Jun. 30, 2016

Related U.S. Application Data

(62) Division of application No. 14/375,450, filed as application No. PCT/EP2013/051930 on Jan. 31, 2013, now Pat. No. 9,309,202.

(30) Foreign Application Priority Data

Feb. 1, 2012 (EP) ..................................... 12356001

(51) Int. Cl.
C07D 231/14 (2006.01)
C07C 229/30 (2006.01)

(52) U.S. Cl.
CPC .......... C07D 231/14 (2013.01); C07C 229/30 (2013.01)

(58) Field of Classification Search
None
See application file for complete search history.

(56) References Cited

U.S. PATENT DOCUMENTS

| | | | |
|---|---|---|---|
| 7,358,387 B2 | 4/2008 | Lantzsch et al. |
| 7,521,397 B2 | 4/2009 | Dunkel et al. |
| 8,586,611 B2 | 11/2013 | Bisaha et al. |
| 2004/0162282 A1 | 8/2004 | Pennell |
| 2009/0042726 A1 | 2/2009 | Black et al. |
| 2009/0326242 A1 | 12/2009 | Pazenok et al. |
| 2011/0028735 A1 | 2/2011 | Pazenok et al. |
| 2013/0197239 A1 | 8/2013 | Pazenok et al. |

FOREIGN PATENT DOCUMENTS

| | | |
|---|---|---|
| JP | 2001192369 A1 | 7/2001 |
| JP | 2009502948 A | 1/2009 |
| JP | 2010083763 A1 | 4/2010 |
| WO | 03070705 A1 | 2/2002 |
| WO | 2005042468 A1 | 5/2005 |
| WO | 2008013925 A2 | 1/2008 |
| WO | 2008022777 A2 | 2/2008 |
| WO | 2008091594 A2 | 7/2008 |
| WO | 2009106230 A2 | 9/2009 |
| WO | 2009112157 A1 | 9/2009 |

OTHER PUBLICATIONS

Database Registry Chemical Abstracts Service, Columbus, Ohio, Accession No. RN 14704-41-7, Entered STN: Nov. 16, 1984.*
Database Registry Chemical Abstracts Service, Columbus, Ohio, Accession No. RN 1335234-35-9, Entered STN: Oct. 13, 2011.*
Database Registry Chemical Abstracts Service, Columbus, Ohio, Accession No. RN 512809-60-8, Entered STN: May 9, 2003.*
Database Registry Chemical Abstracts Service, Columbus, Ohio, Accession No. RN 1394647-33-6, 1394650-76-0, 1394690-57-3, Entered STN: Sep. 18, 2012.*
Database Registry Chemical Abstracts Service, Columbus, Ohio, Accession No. RN 1408069-28-2, Entered STN: Nov. 29, 2012.*
Database Registry Chemical Abstracts Service, Columbus, Ohio, Accession No. RN 1408279-31-1, Entered STN: Nov. 30, 2012.*
Database Registry Chemical Abstracts Service, Columbus, Ohio, Accession No. RN 1046454-44-7, Entered STN: Sep. 4, 2008.*
Database Registry Chemical Abstracts Service, Columbus, Ohio, Accession No. RN 1092769-15-7, Entered STN: Jan. 7, 2009.*
Perevalov V P et al., "Bromination of 4-chloro-1,3,5-trimethylpyrazole", Khimiya Geterotsiklicheskikh Soyedineniy. XP009162800 (1998) No. 1: 40-42.
Extended European Search Report dated Sep. 25, 2012, issued in counterpart European Application No. EP 12 35 6001.
Sloop, et al., "Synthesis of fluorinated heterocycles," J. Fluorine Chem. (2002), vol. 118: 135-147.
Iturrino, et al., "Synthesis, cytostatic and trichomonacide activities of 3,5-bis-(halomethyl)pyrazoles," Eur. J. Med. Chem. (1987), vol. 22: 445-451.
Threadgill, et al., "The reaction of 1,1,1,5,5,5-hexafluoropentane-2,4-dione with hydrazines: a re-investigation," J. of Fluorine Chem. (1993), vol. 65: 21-23.
Pashkevich et al., "Fluoroalkyl containing mono- and bispyrazoles" Zhurnal Vsesoyuznogo Khimicheskogo Obshchestva. pp. 105-107, 1981.
Becker et al., Helvetica Chimica Acta. vol. 23, No. 149: 1114-1122, 1949.
Gerus et al., Journal of Organic Chemistry. vol. 77: 47-56, 2012.
Yu et al., Journal of Fluorine Chemistry. vol. 84: 65-67, 1997.
Liu et al., Organometallics, XP-00266340. vol. 29: 1457-1464, 2010.
Weingarten et al., Journal of Organic Chemistry. vol. 33, No. 4: 1506-1508, 1968.
International Search Report dated May 15, 2013, issued in counterpart International Application No. PCT/EP2013/051930.

* cited by examiner

*Primary Examiner* — Samantha L Shterengarts
(74) *Attorney, Agent, or Firm* — McBee, Moore, Woodward & Vanik IP, LLC

(57) ABSTRACT

The present invention relates to novel 3,5-bis(fluoroalkyl) pyrazole-4-carboxylic acid derivatives and to a process for preparing 3,5-bis(fluoroalkyl)pyrazole-4-carboxylic acid derivatives and 3,5-bis(fluoroalkyl)pyrazoles.

11 Claims, No Drawings

METHOD FOR PRODUCING 3,5-BIS(FLUOROALKYL)-PYRAZOL-4-CARBOXYLIC ACID DERIVATIVES AND 3,5-BIS(FLUOROALKYL)-PYRAZOLES

CROSS REFERENCE TO RELATED APPLICATIONS

This application is a Divisional application of Ser. No. 14/375,450 filed Jul. 30, 2014, which is a § 371 National Stage application of PCT/EP2013/051930, filed Jan. 31, 2013, which claims priority to EP 12356001.3, filed Feb. 1, 2012; each of which are incorporated by reference in their entireties

BACKGROUND

Field of the Invention

The present invention relates to novel 3,5-bis(fluoroalkyl) pyrazole-4-carboxylic acid derivatives and to a process for preparing 3,5-bis(fluoroalkyl)pyrazole-4-carboxylic acid derivatives and 3,5-bis(fluoroalkyl)pyrazoles.

Description of Related Art

Polyfluoroalkylpyrazolylcarboxylic acid derivatives and 3,5-bis(fluoroalkyl)pyrazoles are valuable precursors of active fungicidal ingredients (cf. WO 03/070705 and WO 2008/013925).

Pyrazolecarboxylic acid derivatives are typically prepared by reacting acrylic acid derivatives having two leaving groups with hydrazines (cf. WO 2009/112157 and WO 2009/106230). WO 2005/042468 discloses a process for preparing 2-dihaloacyl-3-aminoacrylic esters by reacting acid halides with dialkylaminoacrylic esters and subsequent cyclization thereof with alkyl hydrazines. WO 2008/022777 describes a process for preparing 3-dihalomethylpyrazole-4-carboxylic acid derivatives by reacting α,α-difluoroamines in the presence of Lewis acids with acrylic acid derivatives and subsequent reaction thereof with alkyl hydrazines.

3,5-Bis(fluoroalkyl)pyrazoles are prepared by reacting bisperfluoroalkyl diketones (e.g. 1,1,1,5,5,5-hexafluoroacetylacetone) with hydrazines (cf. Pashkevich et al., Zhurnal Vsesoyuznogo Khimicheskogo Obshchestva im. D. I. Mendeleeva (1981), 26(1), 105-7). The yield being only 27-40%. The synthesis, isolation and purification of the polyfluoroalkyl diketones is very complex since the compounds are generally very volatile and highly toxic. 3,5-Bisperfluoroalkylpyrazole-4-carboxylic esters are not known.

SUMMARY

In the light of the prior art described above, it is an object of the present invention to provide a process that does not have the aforementioned disadvantages and hence gives a regioselective route to 3,5-bis(fluoroalkyl)pyrazole-4-carboxylic acid derivatives and 3,5-bis(fluoroalkyl)pyrazoles in high yields.

The object described above was achieved by a process for preparing 3,5-bis(fluoroalkyl)pyrazoles of the formula (Ia) and (Ib)

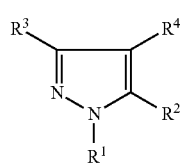

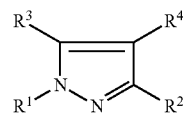

in which $R^1$ is selected from the group comprising H, $C_{1-12}$-alkyl, $C_{3-8}$-cycloalkyl, $C_{6-18}$-aryl, $C_{7-19}$-arylalkyl or $C_{7-19}$-alkylaryl, $CH_2CN$, $CH_2CX_3$, $CH_2COOH$, $CH_2COO$—$(C_{1-12})$-alkyl, and X is independently F, Cl, Br, I;

$R^2$ and $R^3$ is each independently selected from $C_1$-$C_6$-haloalkyl groups;

$R^4$ is selected from the group comprising H, Hal, COOH, (C=O)OR$^5$, CN and (C=O)NR$^5$R$^6$, where $R^5$ and $R^6$ are each independently selected from the group comprising $C_{1-12}$-alkyl, $C_{3-8}$-cycloalkyl, $C_{6-18}$-aryl, $C_{7-19}$-arylalkyl and $C_{7-19}$-alkylaryl, or where $R^5$ and $R^6$ together with the nitrogen atom to which they are bonded may form a five- or six-membered ring;

characterized in that, in step A), α,α-dihaloamines of the formula (II)

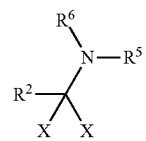

in which X is Cl or F are reacted with a compounds of the formula (III)

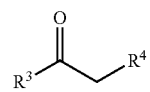

in which the $R^2$ and $R^3$ radicals are each as defined above and, in step B), the product is reacted with hydrazines of the formula (IV)

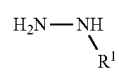

in which $R^1$ is as defined above.

DETAILED DESCRIPTION OF A PREFERRED EMBODIMENT

Surprisingly, the pyrazoles of the formula (I) can be prepared under the inventive conditions with good yields and regioselectivities and in high purity, which means that the process according to the invention overcomes the above-mentioned disadvantages of the preparation processes previously described in the prior art.

Preference is given to the process according to the invention in which the radicals in the compound of the formula (Ia) and (Ib) are defined as follows:

$R^1$ is selected from the group comprising H, $CH_2CN$, $CH_2COO$—$(C_{1-12})$-alkyl, and $R^2$ and $R^3$ are each independently selected from the group comprising $CF_3$, $CF_2H$, $CF_2Cl$;

$R^4$ is selected from the group comprising COOH, (C=O)$OR^5$, CN and (C=O)$NR^5R^6$, where $R^5$ and $R^6$ are each independently selected from the group comprising $C_{1-12}$-alkyl, $C_{3-8}$-cycloalkyl, $C_{6-18}$-aryl, $C_{7-19}$-arylalkyl and $C_{7-19}$-alkylaryl, or where $R^5$ and $R^6$ together with the nitrogen atom to which they are bonded may form a five- or six-membered ring.

Particular preference is given to the process according to the invention in which the radicals in the compound of the formula (Ia) and (Ib) are defined as follows:

$R^1$ is selected is from the group comprising H, $CH_3$, $CH_2COO$—$(C_{1-12})$-alkyl, and $R^2$ and $R^3$ are each independently selected from the group comprising $CF_3$, $CF_2H$, $CF_2Cl$;

$R^4$ is selected from the group comprising COOH, (C=O)$OR^5$.

General Definitions

In the context of the present invention, the term "halogens" (Hal), unless defined differently, comprises those elements which are selected from the group comprising fluorine, chlorine, bromine and iodine, preferably fluorine, chlorine and bromine, more preferably fluorine and chlorine.

Optionally substituted groups may be mono- or polysubstituted, where the substituents in the case of polysubstitutions may be the same or different.

Haloalkyl: straight-chain or branched alkyl groups having 1 to 6 and preferably 1 to 3 carbon atoms (as specified above), where some or all of the hydrogen atoms in these groups may be replaced by halogen atoms as specified above, for example (but not limited to) $C_1$-$C_3$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro, 2-difluoroethyl, 2,2-dichloro-2-fluoroethyl, 2,2,2-trichloroethyl, pentafluoroethyl and 1,1,1-trifluoroprop-2-yl. This definition also applies to haloalkyl as part of a composite substituent, for example haloalkylaminoalkyl etc., unless defined elsewhere. Preference is given to alkyl groups substituted by one or more halogen atoms, for example trifluoromethyl ($CF_3$), difluoromethyl ($CHF_2$), $CF_3CH_2$, $CF_2Cl$ or $CF_3CCl_2$.

Alkyl groups in the context of the present invention, unless defined differently, are linear, branched or cyclic saturated hydrocarbyl groups. The definition $C_1$-$C_{12}$-alkyl encompasses the widest range defined herein for an alkyl group. Specifically, this definition encompasses, for example, the meanings of methyl, ethyl, n-, isopropyl, n-, iso-, sec- and t-butyl, n-pentyl, n-hexyl, 1,3-dimethylbutyl, 3,3-dimethylbutyl, n-heptyl, n-nonyl, n-decyl, n-undecyl or n-dodecyl.

Alkenyl groups in the context of the present invention, unless defined differently, are linear, branched or cyclic hydrocarbyl groups containing at least one single unsaturation (double bond). The definition $C_2$-$C_{12}$-alkenyl encompasses the widest range defined herein for an alkenyl group. Specifically, this definition encompasses, for example, the meanings of vinyl; allyl (2-propenyl), isopropenyl (1-methylethenyl); but-1-enyl (crotyl), but-2-enyl, but-3-enyl; hex-1-enyl, hex-2-enyl, hex-3-enyl, hex-4-enyl, hex-5-enyl; hept-1-enyl, hept-2-enyl, hept-3-enyl, hept-4-enyl, hept-5-enyl, hept-6-enyl; oct-1-enyl, oct-2-enyl, oct-3-enyl, oct-4-enyl, oct-5-enyl, oct-6-enyl, oct-7-enyl; non-1-enyl, non-2-enyl, non-3-enyl, non-4-enyl, non-5-enyl, non-6-enyl, non-7-enyl, non-8-enyl; dec-1-enyl, dec-2-enyl, dec-3-enyl, dec-4-enyl, dec-5-enyl, dec-6-enyl, dec-7-enyl, dec-8-enyl, dec-9-enyl; undec-1-enyl, undec-2-enyl, undec-3-enyl, undec-4-enyl, undec-5-enyl, undec-6-enyl, undec-7-enyl, undec-8-enyl, undec-9-enyl, undec-10-enyl; dodec-1-enyl, dodec-2-enyl, dodec-3-enyl, dodec-4-enyl, dodec-5-enyl, dodec-6-enyl, dodec-7-enyl, dodec-8-enyl, dodec-9-enyl, dodec-10-enyl, dodec-11-enyl; buta-1,3-dienyl or penta-1,3-dienyl.

Alkynyl groups in the context of the present invention, unless defined differently, are linear, branched or cyclic hydrocarbyl groups containing at least one double unsaturation (triple bond). The definition $C_2$-$C_{12}$-alkynyl encompasses the widest range defined herein for an alkynyl group. Specifically, this definition encompasses, for example, the meanings of ethynyl (acetylenyl); prop-1-ynyl and prop-2-ynyl.

Cycloalkyl: monocyclic, saturated hydrocarbyl groups having 3 to 8 and preferably 3 to 6 carbon ring members, for example (but not limited to) cyclopropyl, cyclopentyl and cyclohexyl. This definition also applies to cycloalkyl as part of a composite substituent, for example cycloalkylalkyl etc., unless defined elsewhere.

Aryl groups in the context of the present invention, unless defined differently, are aromatic hydrocarbyl groups which may have one, two or more heteroatoms selected from O, N, P and S. The definition $C_{6-18}$-aryl encompasses the widest range defined herein for an aryl group having 5 to 18 skeleton atoms, where the carbon atoms may be exchanged for heteroatoms. Specifically, this definition encompasses, for example, the meanings of phenyl, cycloheptatrienyl, cyclooctatetraenyl, naphthyl and anthracenyl; 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl; 1-pyrrolyl, 1-pyrazolyl, 1,2,4-triazol-1-yl, 1-imidazolyl, 1,2,3-triazol-1-yl, 1,3,4-triazol-1-yl; 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

Arylalkyl groups (aralkyl groups) in the context of the present invention, unless defined differently, are alkyl groups which are substituted by aryl groups, may have one $C_{1-8}$-alkylene chain and may have, in the aryl skeleton, one or more heteroatoms selected from O, N, P and S. The definition $C_{7-19}$-aralkyl group encompasses the widest range defined herein for an arylalkyl group having a total of 7 to 19 atoms in the skeleton and alkylene chain. Specifically, this definition encompasses, for example, the meanings of benzyl and phenylethyl.

Alkylaryl groups (alkaryl groups) in the context of the present invention, unless defined differently, are aryl groups which are substituted by alkyl groups, may have one $C_{1-8}$-alkylene chain and may have, in the aryl skeleton, one or more heteroatoms selected from O, N, P and S. The definition $C_{7-19}$-alkylaryl group encompasses the widest range defined herein for an alkylaryl group having a total of 7 to 19 atoms in the skeleton and alkylene chain Specifically, this definition encompasses, for example, the meanings of tolyl or 2,3-, 2,4-, 2,5-, 2,6-, 3,4- or 3,5-dimethylphenyl.

The term intermediate used in the context of the present invention describes the substances which occur in the process according to the invention and are prepared for further chemical processing and are consumed or used therein in order to be converted to another substance. The intermediates can often be isolated and intermediately stored or are used without prior isolation in the subsequent reaction step. The term "intermediate" also encompasses the generally unstable and short-lived intermediates which occur transiently in multistage reactions (staged reactions) and to which local minima in the energy profile of the reaction can be assigned.

The inventive compounds may be present as mixtures of any different isomeric forms possible, especially of stereoisomers, for example E and Z isomers, threo and erythro isomers, and optical isomers, but if appropriate also of tautomers. Both the E and the Z isomers are disclosed and claimed, as are the threo and erythro isomers, and also the optical isomers, any mixtures of these isomers, and also the possible tautomeric forms.

The process is illustrated in Scheme 1:

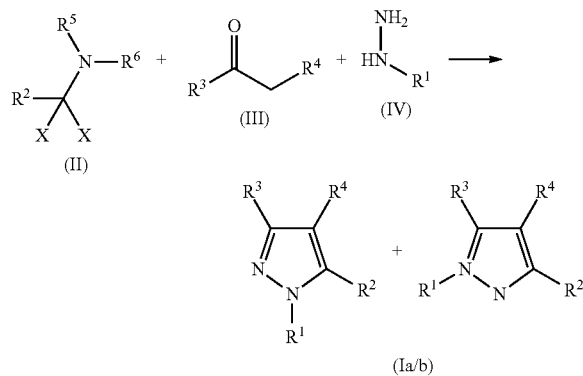

The present invention likewise provides 3,5-bis(fluoroalkyl)pyrazoles of the formula (Ia) or (Ib)

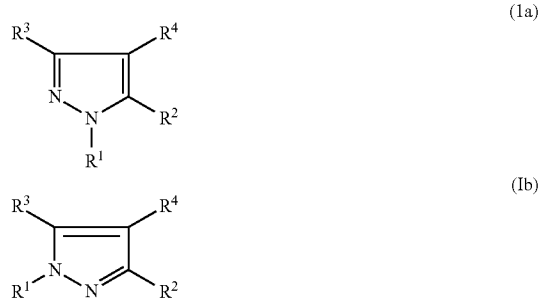

in which
R$^1$ is selected from H, C$_{1-12}$-alkyl, C$_{3-8}$-cycloalkyl, C$_{6-18}$-aryl, C$_{7-19}$-arylalkyl or C$_{7-19}$-alkylaryl, CH$_2$CN, CH$_2$CX$_3$, CH$_2$COOH, CH$_2$COO—(C$_{1-12}$)-alkyl;
X is independently F, Cl, Br, I;
R$^2$ and R$^3$ is selected from C$_1$-C$_6$-haloalkyl groups,
R$^4$ is selected from the group of H, F, Cl, Br, COOH, (C═O)OR$^5$, CN and (C═O)NR$^5$R$^6$, where R$^5$ and R$^6$ are each independently selected from the group comprising C$_{1-12}$-alkyl, C$_{3-8}$-cycloalkyl, C$_{6-18}$-aryl, C$_{7-19}$-arylalkyl and C$_{7-19}$-alkylaryl, or where R$^5$ and R$^6$ together with the nitrogen atom to which they are bonded may form a five- or six-membered ring.

In a preferred embodiment of the present invention, the radicals in formula (Ia) and (Ib) are defined as follows:
R$^1$ is selected from H, methyl, —CH$_2$COOH, CH$_2$COOR$^5$, CH$_2$CN, CH$_2$CX$_3$:
X is independently F, Cl;
R$^2$ and R$^3$ are selected from difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro, 2-difluoroethyl, 2,2-dichloro-2-fluoroethyl, 2,2,2-trichloroethyl, pentafluoroethyl and 1,1,1-trifluoroprop-2-yl;
R$^4$ is selected from the group comprising H, Br, COOCH$_3$, COOEt, COOC$_3$H$_7$, CN and CONMe$_2$, CONEt$_2$.

In a particularly preferred embodiment of the present invention, the radicals in formula (Ia) and (Ib) are defined as follows:
R$^1$ is selected from H, CH$_2$COOH, CH$_2$COOMe, CH$_2$CN,
R$^2$ and R$^3$ are selected from the group consisting of trifluoromethyl, difluoromethyl, difluorochloromethyl, pentafluoroethyl;
R$^4$ is selected from the group consisting of H, Br, COOH.

Very particular preference is given to compounds of the general formula (I) in which
R1=H; R$^2$=R$^3$=CF$_2$H and R$^4$=COOEt or
R$^1$=H; R$^2$=R$^3$=CF$_2$H and R$^4$=COOH or
R$^1$=CH$_2$COOEt; R$^2$=R$^3$=CF$_2$H and R$^4$=COOEt.

Process Description

Scheme 2:

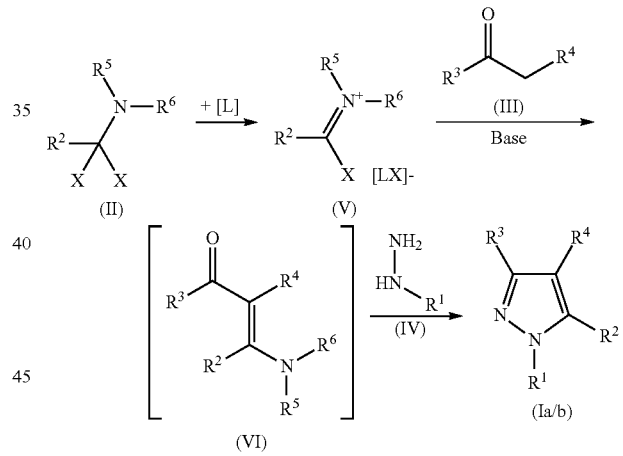

In one embodiment of the process according to the invention, in step A), α,α-dihaloamines of the formula (II) are first reacted, optionally in the presence of a Lewis acid [L], with compounds of the formula (III).

Preferred compounds of the general formula (II) are 1,1,2,2-tetrafluoroethyl-N,N-dimethylamine (TFEDMA), 1,1,2,2-tetrafluoroethyl-N,N-diethylamine, 1,1,2-trifluoro-2-(trifluoromethyl)ethyl-N,N-dimethylamine, 1,1,2-trifluoro-2-(trifluoromethyl)ethyl-N,N-diethylamine (Ishikawa's reagent), 1,1,2-trifluoro-2-chloroethyl-N,N-dimethylamine and 1,1,2-trifluoro-2-chloroethyl-N,N-diethylamine (Yarovenko's reagent).

Compounds of the general formula (II) are used as aminoalkylating agents. Preference is given to 1,1,2,2-tetrafluoroethyl-N,N-dimethylamine (TFEDMA) and 1,1,2,2-tetrafluoroethyl-N,N-diethylamine, and particular preference to 1,1,2,2-tetrafluoroethyl-N,N-dimethylamine α,α-Dihaloamines such as TFEDMA and Ishikawa's reagent are commercially available or can be prepared (cf. Yarovenko et al., Zh. Obshch. Khim 1959, 29, 2159, Chem. Abstr. 1960, 54, 9724h or Petrov et al., J. Fluor. Chem. 109 (2011) 25-31).

Yagnpolskii et al. (Zh. Organicheskoi Khim (1978), 14(12), 2493-6) shows that the reaction of Yarovenko's reagent ($FClCHCF_2NEt_2$) with nitriles of the formula $RCH_2CN$ (R=CN, $CO_2Et$) affords the derivatives of the formula $(NC)RC=C(NEt_2)CHFCl$ in approx. 70% yield. Keto compounds of the formula (III) do not react with α,α-dihaloamines of the formula (II) under this condition.

Petrov et al. (J. of Fluorine Chem. (2011), 132(12), 1198-1206) shows that TFEDMA ($HCF_2CF_2NMe_2$) reacts with cyclic β-diketones to transfer a difluoroacetyl group.

In a preferred embodiment of the process according to the invention, the α,α-dihaloamine is first reacted with Lewis acid [L], for example $BF_3$, $AlCl_3$, $SbCl_5$, $SbF_5$, $ZnCl_2$, and then the mixture of the compound of the formula (III) and a base is added, in substance or dissolved in a suitable solvent (cf. WO 2008/022777).

α,α-Dihaloamines are reacted with Lewis acids (preparation of the imminium salts of the formula (V)) according to the teaching of WO 2008/022777. According to the invention, the reaction is effected at temperatures of 20° C. to +40° C., preferably at temperatures of 20° C. to +30° C., more preferably at −10 to 20° C. and under standard pressure. Due to the hydrolysis sensitivity of the α,α-dihaloamines, the reaction is conducted in anhydrous apparatuses under inert gas atmosphere.

The reaction time is not critical and may, according to the batch size and temperature, be selected within a range between a few minutes and several hours.

According to the invention, 1 mol of the Lewis acid [L] is reacted with equimolar amounts of the α,α-dihaloamine of the formula (II).

The aminoalkylation (reaction with compound of the formula (II)) is preferably effected in the presence of a base. Preference is given to organic bases such as trialkylamines, pyridines, alkylpyridines, phosphazenes and 1,8-diazabicyclo[5.4.0]undecene (DBU); alkali metal hydroxides, for example lithium hydroxide, sodium hydroxide or potassium hydroxide, alkali metal carbonates ($Na_2CO_3$, $K_2CO_3$) and alkoxides, for example NaOMe, NaOEt, NaOt-Bu, KOt-Bu or KF.

For the process according to the invention, 1 to 5, preferred 1,5 to 4 most preferred 2 to 3.5 mol of the base for the compound of the formula (III) is reacted with equimolar amounts of the α,α-dihaloamine of the formula (II).

Preference is given to using keto compounds of the formula (III) selected from the group comprising ethyl 4,4,4-trifluoro-3-oxobutanoates, methyl 4,4,4-trifluoro-3-oxobutanoates, ethyl 4,4-difluoro-3-oxobutanoates, ethyl 4-chloro-4,4-difluoro-3-oxobutanoates, 1,1,1-trifluoroacetone or 4-chloro-4,4-difluoro-3-oxobutanenitriles.

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide; sulphoxides such as dimethyl sulphoxide or sulphones such as sulpholane. Particular preference is given, for example, to THF, acetonitriles, ethers, toluene, xylene, chlorobenzene, n-hexane, cyclohexane or methylcyclohexane, and very particular preference, for example, to acetonitrile, THF, ether or dichloromethane The intermediates of the formula (VI) formed can be used in the cyclization step with hydrazines without prior workup.

Alternatively, the intermediates can be isolated and characterized by suitable workup steps and optionally further purification.

Step B) Cyclization

The cyclization in step B) by reaction with compound (IV) in the process according to the invention is effected at temperatures of −40° C. to +80° C., preferably at temperatures of −10° C. to +60° C., more preferably at −10 to 50° C. and under standard pressure.

The reaction time is not critical and may, according to the batch size, be selected within a relatively wide range.

Typically, the cyclization step B) is effected without changing the solvent.

According to the invention, 1 to 2 mol, preferably 1 to 1.5, of the hydrazines of the formula (IV) per 1 mol of the compound of the formula (III) are used.

Preference is given to performing all reaction steps of the process according to the invention in the same solvent. In the context of the present invention, for example, hydrazine hydrate, methyl hydrazine, ethyl hydrazines, phenyl hydrazines, tert-butyl hydrazines, methyl- or ethylhydrazinoacetate hydrochlorides or hydrazinoacetonitrile hydrochloride are used.

Said hydrazines of the formula (IV) are commercially available or can be prepared as described, for example, in Niedrich et al., Journal fuer Praktische Chemie (Leipzig) (1962), 17 273-81; Carmi, A.; Pollak, Journal of Organic Chemistry (1960), 25 44-46.

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; alcohols such as methanol, ethanol, isopropanol or butanol, nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide; sulphoxides such as dimethyl sulphoxide or sulphones such as sulpholane. Particular preference is given, for example, to acetonitrilestoluene, xylene, chlorobenzene, n-hexane, cyclohexane or methylcyclohexane, and very particular preference, for example, to acetonitriles, THF, toluene or xylene. After the reaction has ended, for example, the solvents are removed and the product is isolated by filtration, or the product is first washed with water and extracted, the organic phase is removed and the solvent is removed under reduced pressure.

The compounds of the formula (I) where $R^4$=$COOR^5$ can then be converted to pyrazole acids of the formula (I) $R^4$=COOH.

The conversion is generally performed under acidic or basic conditions.

For acidic hydrolysis, preference is given to mineral acids, for example $H_2SO_4$, HCl, $HSO_3Cl$, HF, HBr, HI, $H_3PO_4$ or organic acids, for example $CF_3COOH$, p-toluenesulphonic acid, methanesulphonic acid, trifluoromethanesulphonic acid. The reaction can be accelerated by the addition of catalysts, for example $FeCl_3$, $AlCl_3$, $BF_3$, $SbCl_3$, $NaH_2PO_4$. The reaction can likewise be performed without addition of acid, only in water.

Basic hydrolysis is effected in the presence of inorganic bases such as alkali metal hydroxides, for example lithium hydroxide, sodium hydroxide or potassium hydroxide, alkali metal carbonates, for example $Na_2CO_3$, $K_2CO_3$ and alkali metal acetates, for example NaOAc, KOAc, LiOAc, and alkali metal alkoxides, for example NaOMe, NaOEt, NaOt-Bu, KOt-Bu of organic bases such as trialkylamines, alkylpyridines, phosphazenes and 1,8-diazabicyclo[5.4.0]undecene (DBU). Preference is given to the inorganic bases, for example NaOH, KOH, $Na_2CO_3$ or $K_2CO_3$.

Preference is given to conversion by means of basic hydrolysis.

The process step of the invention is performed preferably within a temperature range from 20° C. to +150° C., more preferably at temperatures of 30° C. to +110° C., most preferably at 30 to 80° C.

The process step of the invention is generally performed under standard pressure. Alternatively, however, it is also possible to work under vacuum or under elevated pressure (for example reaction in an autoclave with aqueous HCl).

The reaction time may, according to the batch size and the temperature, be selected within a range between 1 hour and several hours.

The reaction step can be performed in substance or in a solvent. Preference is given to performing the reaction in a solvent. Suitable solvents are, for example, selected from the group comprising water, alcohols such as methanol, ethanol, isopropanol or butanol, aliphatic and aromatic hydrocarbons, for example n-hexane, benzene or toluene, which may be substituted by fluorine and chlorine atoms, such as methylene chloride, dichloroethane, chlorobenzene or dichlorobenzene; ethers, for example diethyl ether, diphenyl ether, methyl tert-butyl ether, isopropyl ethyl ether, dioxane, diglyme, dimethylglycol, dimethoxyethane (DME) or THF; nitriles such as methyl nitrile, butyl nitrile or phenyl nitrile; amides we dimethylformamide (DMF) or N-methylpyrrolidone (NMP) or mixtures of such solvents, particular preference being given to water, acetonitrile, dichloromethane and alcohols (ethanol).

The inventive compounds (Ia) and (Ib) are used for preparation of active fungicidal ingredients.

The present invention likewise provides compound of the formula (VI)

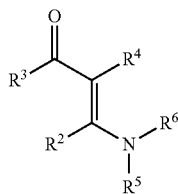

in which
R² and R³ are each independently selected from the group comprising $CF_3$, $CF_2H$, $CF_2Cl$;
R⁴ is selected from the group comprising (C=O)OR⁵;
R⁵ and R⁶ are each independently selected from the group comprising $C_{1-6}$-alkyl.

The process according to the invention is described further in the examples which follow. However, the examples should not be interpreted in a restrictive manner.

Characterization of the Intermediate Compound (YI)

Ethyl 2-(2-chloro-2,2-difluoroacetyl)-3-(dimethylamino)-4,4-difluorobut-2-enoate $BF_3.OEt_2$ (0.12 ml, 1.0 mmol) was added to a solution of TFEDMA (0.12 ml, 1.0 mmol) in dry dichloromethane (1 ml) under argon in a Teflon flask. The solution was stirred at room temperature for 15 min. before the dichloromethane was removed under reduced pressure. The residue was then taken up in perdeuterated acetonitrile (1 ml). In a second Teflon flask, ethyl 4-chloro-4,4-difluoroacetoacetate (0.20 g, 1.0 mmol) was added to a solution of potassium fluoride (0.18 g, 3.0 mmol) in CD3CN (2 ml) and the mixture was stirred at room temperature for 15 min. To this were then added dropwise, at −30° C., the contents of the first Teflon flask, and the reaction mixture was stirred at room temperature overnight and then analysed by ¹H and ¹³C NMR spectroscopy. The intermediate compound (ethyl 2-(2-chloro-2,2-difluoroacetyl)-3-(dimethylamino)-4,4-difluorobut-2-enoate) was characterized as a 2:1 mixture (¹H NMR) in the presence of ethyl 3-(dimethylamino)-4,4-difluorobut-2-enoate.

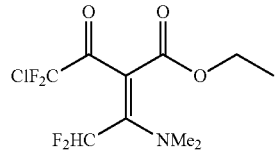

¹H NMR (CD₃CN, 300 MHz, 25° C.): δ=6.36 (t, 1H, CHF₂, $J_{H\text{-}F}$=53.2 Hz), 4.21 (q, 2H, CH₂, J=7.2 Hz), 3.07 (t, 3H, NMe, $J_{H\text{-}F}$=1.2 Hz), 2.95 (t, 3H, NMe, $J_{H\text{-}F}$=1.2 Hz), 1.26 (t, 3H, CH₃, J=7.2 Hz) ppm.

¹³C NMR (CD₃CN, 75 MHz, 25° C.): δ=185.3 (F₂ClC—CO), 164.9 (CO), 161.7 (t, $\underline{C}_{IV}$—NMe₂, $J_{C\text{-}F}$=25.1 Hz), 119.4 (t, CF₂Cl, $J_{C\text{-}F}$=304.3 Hz), 108.1 (t, CHF₂, $J_{C\text{-}F}$=244.4 Hz), 98.1 (t, $C_{IV}$, $J_{C\text{-}F}$=4.8 Hz), 61.9 (CH₂), 35.0 (N-Me₂), 13.3 (CH₃) ppm.

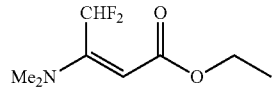

¹H NMR (CD₃CN, 300 MHz, 25° C.): δ=6.65 (t, 1H, CHF₂, $J_{H\text{-}F}$=51.9 Hz), 5.70 (s, 1H, CH), 4.31 (q, 2H, CH₂, J=7.1 Hz), 3.91 (t, 3H, NMe, $J_{H\text{-}F}$=0.8 Hz), 3.22 (t, 3H, NMe, $J_{H\text{-}F}$=1.2 Hz), 1.31 (t, 3H, CH₃, J=7.1 Hz) ppm.

¹³C NMR (CD₃CN, 75 MHz, 25° C.): δ=171.3 (CO), 163.4 (t, $\underline{C}_{IV}$—NMe₂, $J_{C\text{-}F}$=21.3 Hz), 110.5 (t, CHF₂, $J_{C\text{-}F}$=246.7 Hz), 91.1 (t, $C_{IV}$, $J_{C\text{-}F}$=4.4 Hz), 61.2 (CH₂), 36.4 (N-Me₂), 13.3 (CH₃) ppm.

PREPARATION EXAMPLES

Example 1

N-Methyl-3-difluoromethyl-5-trifluoromethyl-4-pyrazolecarboxylic acid ethyl ester

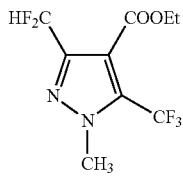

BF$_3$·OEt$_2$ (0.62 ml, 5.0 mmol) was added to a solution of TFEDMA (0.59 ml, 5.0 mmol) in dry dichloromethane (5 ml) under argon in a Teflon flask. The solution was stirred at room temperature for 15 min, before the dichloromethane was removed under reduced pressure. The residue was then taken up in dry acetonitrile (5 ml). In a second Teflon flask, ethyl 4,4,4-trifluoroacetoacetate (0.73 ml, 5.0 mmol) was added to a solution of potassium fluoride (0.88 g, 15.0 mmol) in dry acetonitrile (10 ml) and the mixture was stirred at room temperature for 15 min. To this were added dropwise, at −30° C. the contents of the first flask. The reaction mixture was brought to room temperature in the cold bath and stirred overnight. Methyl hydrazine (0.32 ml, 6.0 mmol) was then added dropwise at room temperature and the mixture was stirred overnight. The solvent was removed under reduced pressure and the residue was purified by flash chromatography on silica gel with a pentanes/diethyl ether mixture (9:1-8:2). N-Methyl-3-difluoromethyl-5-trifluoromethyl-4-pyrazolecarboxylic acid ethyl ester (0.99 g, 3.64 mmol, 73%) was obtained as a yellow oil.

$^1$H NMR (CDCl$_3$, 300 MHz, 25° C.): δ=7.00 (t, 1H, CHF$_2$, J$_{H-F}$=54 Hz), 4.37 (q, 2H, CH$_2$, J=7.2 Hz), 4.12 (s, 3H, N—CH$_3$), 1.37 (t, 3H, CH$_3$, J=7.2 Hz) ppm. $^{13}$C NMR (CDCl$_3$, 75 MHz, 25° C.): δ=160.2 (CO), 145.7 (t, C$_{IV}$arom, J$_{C-F}$=25.6 Hz), 133.2 (q, C$_{IV}$arom, J$_{C-F}$=40.3 Hz), 119.0 (q, CF$_3$, J$_{C-F}$=271.2 Hz), 114.4 (C$_{IV}$arom), 109.0 (t, CHF$_2$, J$_{C-F}$=237.9 Hz), 61.9 (CH$_2$), 40.8 (q, N—CH$_3$, J$_{C-F}$=3.2 Hz), 13.8 (CH$_3$) ppm. $^{19}$F NMR (CDCl$_3$, 282 MHz, 25° C.): δ=−57.6 (CF$_3$), −116.4 (CHF$_2$) ppm.

Example 2

As Example 1: except that pyridine was used instead of potassium fluoride. The yield is 63%.

Example 3

N-Methyl-3-difluoromethyl-5-trifluoromethyl-4-pyrazolecarboxylic acid

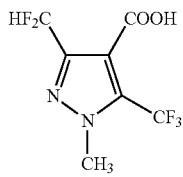

N-Methyl-3-difluoromethyl-5-trifluoromethyl-4-pyrazolecarboxylic acid ethyl ester (0.5 g, 1.84 mmol) in ethanol (3 ml) was admixed gradually with an 8N aqueous sodium hydroxide solution (0.7 ml) and stirred at room temperature for 3 h. The solvent was removed by rotary evaporation; the residue was taken up in water (10 ml) and extracted with diethyl ether (10 ml). Acidification to pH 1 with 1M HCl was followed by extraction with ethyl acetate (3×10 ml). The combined organic phases were dried over sodium sulphate and filtered, and the solvent was removed by rotary evaporation. N-Methyl-3-difluoromethyl-5-trifluoromethyl-4-pyrazolecarboxylic acid (0.44 g, 1.80 mmol, 98%) was isolated as a yellowish solid.

$^1$H NMR (CDCl$_3$, 300 MHz, 25° C.): δ=7.08 (t, 1H, CHF$_2$, J$_{H-F}$=53.5 Hz), 4.16 (s, 3H, N—CH$_3$) ppm. $^{13}$C NMR (CDCl$_3$, 75 MHz, 25° C.): δ=165.5 (CO), 146.7 (t, C$_{IV}$arom, J$_{C-F}$=18.8 Hz), 134.4 (q, C$_{IV}$arom, J$_{C-F}$=30.8 Hz), 118.8 (q, CF$_3$, J$_{C-F}$=202.5 Hz), 112.9 (C$_{IV}$arom), 108.7 (t, CHF$_2$, J$_{C-F}$=177.0 Hz), 41.1 (q, N—CH$_3$, J$_{C-F}$=2.3 Hz) ppm. $^{19}$F NMR (CDCl$_3$, 282 MHz, 25° C.): δ=−57.9 (CF$_3$), −117.3 (CHF$_2$, J$_{F-H}$=53.5 Hz) ppm.

Example 4

N—H-3-Difluoromethyl-5-trifluoromethyl-4-pyrazolecarboxylic acid ethyl ester

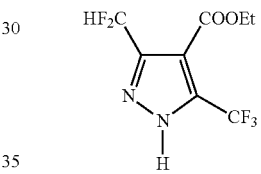

BF$_3$·OEt$_2$ (0.31 ml, 2.5 mmol) was added to a solution of TFEDMA (0.30 ml, 2.5 mmol) in dry dichloromethane (2.5 ml) under argon in a Teflon flask. The solution was stirred at room temperature for 15 min, before the dichloromethane was removed under reduced pressure. The residue was then taken up in dry acetonitrile (2.5 ml). In a second Teflon flask, ethyl 4,4,4-trifluoroacetoacetate (0.37 ml, 2.5 mmol) was added to a solution of potassium fluorides (0.44 g, 7.5 mmol) in dry acetonitrile (5 ml) and the mixture was stirred at room temperature for 15 min. To this were added dropwise, at −30° C., the contents of the first flask. The reaction mixture was brought to room temperature in the cold bath and stirred overnight. Hydrazine hydrate (0.15 ml, 3.0 mmol) was then added dropwise at room temperature and the mixture was stirred for 24 h. The solvent was removed under reduced pressure and the residue was purified by flash chromatography on silica gel with a pentanes/diethyl ether mixture (9:1-7:3). N—H-3-Difluoromethyl-5-trifluoromethyl-4-pyrazolecarboxylic acid ethyl ester (0.48 g, 1.88 mmol, 75%) was obtained as a yellowish oil, which crystallized when left to stand.

$^1$H NMR (CDCl$_3$, 300 MHz, 25° C.): δ=11.07 (brs, 1H, NH), 7.22 (t, 1H, CHF$_2$, J$_{H-F}$=53.5 Hz), 4.39 (q, 2H, CH$_2$, J=6.9 Hz), 1.38 (t, 3H, CH$_3$, J=6.9 Hz) ppm. $^{13}$C NMR (CDCl$_3$, 75 MHz, 25° C.): δ=160.4 (CO), 142.2 (t, C$_{IV}$arom, J$_{C-F}$=18.3 Hz), 142.2 (q, C$_{IV}$arom, J$_{C-F}$=32.0 Hz), 119.7 (q, CF$_3$, J$_{C-F}$=268.1 Hz), 111.7 (C$_{IV}$arom), 107.4 (t, CHF$_2$, J$_{C-F}$=237.5 Hz), 62.0 (CH$_2$), 13.7 (CH$_3$) ppm. $^{19}$F NMR (CDCl$_3$, 282 MHz, 25° C.): δ=−62.5 (CF$_3$), −117.1 (CHF$_2$, J$_{F-H}$=53.5 Hz) ppm.

Example 5

As Example 3: except that pyridine was used instead of potassium fluoride. The yield is 67%.

Example 6

N-Methyl-3,5-bis(difluoromethyl)-4-pyrazolecarboxylic acid ethyl ester

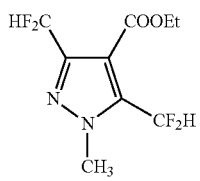

$BF_3 \cdot OEt_2$ (1.24 ml, 10.0 mmol) was added to a solution of TFEDMA (1.20 ml, 10.0 mmol) in dry dichloromethane (10 ml) under argon in a Teflon flask. The solution was stirred at room temperature for 15 min, before the dichloromethane was removed under reduced pressure. The residue was then taken up in dry acetonitrile (10 ml). In a second Teflon flask, ethyl 4,4-difluoroacetoacetate (1.03 ml, 10.0 mmol) was added to a solution of pyridine (1.6 ml, 20.0 mmol) in dry acetonitrile (20 ml) and the mixture was stirred at room temperature for 15 min. To this were added dropwise, at −30° C., the contents of the first flask. The reaction mixture was brought to room temperature in the cold bath and stirred overnight. Methyl hydrazine (0.79 ml, 15.0 mmol) was then added dropwise at room temperature and the mixture was stirred overnight. The solvent was removed under reduced pressure and the residue was purified by flash chromatography on silica gel with a pentanes/diethyl ether mixture (10:0-8:2). (10:0 to 8:2). N-Methyl-3,5-difluoromethyl-4-pyrazolecarboxylic acid ethyl ester (1.75 g, 6.89 mmol, 69%) was obtained as a colourless oil, which crystallized when left to stand.

$^1$H NMR (CDCl$_3$, 300 MHz, 25° C.): δ=7.48 (t, 1H, CHF$_2$, $J_{H\text{-}F}$=52.6 Hz), 7.04 (t, 1H, CHF$_2$, $J_{H\text{-}F}$=53.8 Hz), 4.38 (q, 2H, CH$_2$, J=7.1 Hz), 4.12 (s, 3H, N—CH$_3$), 1.39 (t, 3H, CH$_3$, J=7.2 Hz) ppm. $^{13}$C NMR (CDCl$_3$, 75 MHz, 25° C.): δ=161.1 (CO), 145.3 (t, C$_{IV}$arom, $J_{C\text{-}F}$=24.9 Hz), 138.2 (t, C$_{IV}$arom, $J_{C\text{-}F}$=24.1 Hz), 112.9 (m, C$_{IV}$arom), 109.1 (t, CHF$_2$, $J_{C\text{-}F}$=237.6 Hz), 107.2 (t, CHF$_2$, $J_{C\text{-}F}$=236.3 Hz), 61.5 (CH$_2$), 39.6 (t, N—CH, $J_{C\text{-}F}$=3.1 Hz), 13.9 (CH$_3$) ppm. $^{19}$F NMR (CDCl$_3$, 282 MHz, 25° C.): δ=−117.00 (CHF$_2$, $J_{F\text{-}H}$=53.8 Hz), −117.04 (CHF$_2$, $J_{F\text{-}H}$=52.6 Hz) ppm.

Example 7

N-Methyl-3,5-bis(difluoromethyl)-4-pyrazolecarboxylic acid

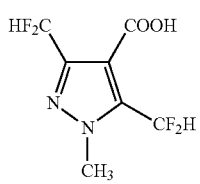

N-Methyl-3,5-difluoromethyl-4-pyrazolecarboxylic acid ethyl ester (0.5 g, 2.0 mmol) in ethanol (3 ml) was admixed gradually with an 8N aqueous sodium hydroxide solution (0.8 ml) and stirred at room temperature for 2 h. The solvent was removed by rotary evaporation; the residue was taken up in water (10 ml) and extracted with diethyl ether (10 ml). Acidification to pH 1 with 6M HCl was followed by extraction with ethyl acetate (3×10 ml). The combined organic phases were dried over sodium sulphate and filtered, and the solvent was removed by rotary evaporation. N-Methyl-3,5-difluoromethyl-4-pyrazolecarboxylic acid (0.44 g, 1.95 mmol, 97%) was isolated as a colourless solid.

$^1$H NMR (CDCl$_3$, 300 MHz, 25° C.): δ=12.16 (brs, 1H, COOH), 7.48 (t, 1H, CHF$_2$, $J_{H\text{-}F}$=52.4 Hz), 7.08 (t, 1H, CHF$_2$, $J_{H\text{-}F}$=53.6 Hz), 4.16 (s, 3H, N—CH$_3$) ppm. $^{13}$C NMR (CDCl$_3$, 75 MHz, 25° C.): δ=166.9 (CO), 146.4 (t, C$_{IV}$arom, $J_{C\text{-}F}$=25.1 Hz), 139.2 (t, C$_{IV}$arom, $J_{C\text{-}F}$=24.4 Hz), 111.5 (C$_{IV}$arom), 108.8 (t, CHF$_2$, $J_{C\text{-}F}$=238.1 Hz), 106.9 (t, CHF$_2$, $J_{C\text{-}F}$=237.0 Hz), 39.9 (t, N—CH$_3$, $J_{C\text{-}F}$=3.1 Hz) ppm. $^{19}$F NMR (CDCl$_3$, 282 MHz, 25° C.): δ=−117.1 (CHF$_2$, $J_{F\text{-}H}$=52.6 Hz), −117.3 (CHF$_2$, $J_{F\text{-}H}$=53.7 Hz) ppm.

Example 8

N—H-3,5-Bis(difluoromethyl)-4-pyrazolecarboxylic acid ethyl ester

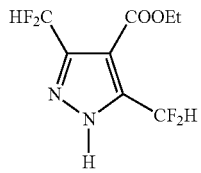

$BF_3 \cdot OEt_2$ (1.85 ml, 15.0 mmol) was added to a solution of TFEDMA (1.76 ml, 15.0 mmol) in dry dichloromethane (15 ml) under argon in a Teflon flask. The solution was stirred at room temperature for 15 min, before the dichloromethane was removed under reduced pressure. The residue was then taken up in dry acetonitrile (15 ml). In a second Teflon flask, ethyl 4,4-difluoroacetoacetate (1.55 ml, 15 mmol) was added to a solution of potassium fluorides (2.61 g, 45 mmol) in dry acetonitrile (30 ml) and the mixture was stirred at room temperature for 15 min. To this were added dropwise, at −30° C., the contents of the first flask. The reaction mixture was brought to room temperature in the cold bath and stirred overnight. Hydrazine hydrate (1.1 ml, 22.5 mmol) was then added dropwise at room temperature and the mixture was stirred overnight. The solvent was removed under reduced pressure and the residue was purified by flash chromatography on silica gel with a pentanes/diethyl ether mixture (9:1-7:3). N—H-3,5-Difluoromethyl-4-pyrazolecarboxylic acid ethyl ester (2.02 g, 8.40 mmol, 56%) was isolated as a colourless solid.

$^1$H NMR (CDCl$_3$, 300 MHz, 25° C.): δ=7.15 (t, 2H, CHF$_2$, $J_{H\text{-}F}$=53.6 Hz), 4.39 (q, 2H, CH$_2$, J=7.1 Hz), 1.39 (t, 3H, CH$_3$, J=7.1 Hz) ppm. $^{13}$C NMR (CDCl$_3$, 75 MHz, 25° C.): δ=161.1 (CO), 143.8 (t, C$_{IV}$arom, $J_{C\text{-}F}$=23.1 Hz), 111.6 (C$_{IV}$arom), 108.2 (t, CHF$_2$, $J_{C\text{-}F}$=238.4 Hz), 61.7 (CH$_2$), 13.9 (CH$_3$) ppm. $^{19}$F NMR (CDCl$_3$, 282 MHz, 25° C.): δ=−117.3 (CHF$_2$, $J_{F\text{-}H}$=53.6 Hz) ppm.

Example 9

As Example 8: except that pyridine was used instead of potassium fluoride. The yield is 29%.

Example 10

N-Methyl-3-difluoromethyl-5-chlorodifluoromethyl-4-pyrazolecarboxylic acid ethyl ester

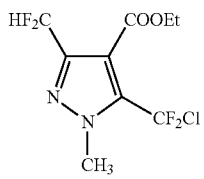

BF$_3$.OEt$_2$ (1.24 ml, 10.0 mmol) was added to a solution of TFEDMA (1.20 ml, 10.0 mmol) in dry dichloromethane (10 ml) under argon in a Teflon flask. The solution was stirred at room temperature for 15 min, before the dichloromethane was removed under reduced pressure. The residue was then taken up in dry acetonitrile (10 ml). In a second Teflon flask, ethyl 4-chloro-4,4-difluoroacetoacetate (2.0 g, 10.0 mmol) was added to a solution of pyridine (2.42 ml, 30.0 mmol) in dry acetonitrile (20 ml) and the mixture was stirred at room temperature for 15 min. To this were added dropwise, at −30° C., the contents of the first flask. The reaction mixture was brought to room temperature in the cold bath and stirred overnight. Methyl hydrazine (0.79 ml, 15.0 mmol) was then added dropwise at room temperature and the mixture was stirred overnight. The solvent was removed under reduced pressure and the residue was purified by flash chromatography on silica gel with a pentanes/diethyl ether mixture (10:0-8:2). N-Methyl-3-difluoromethyl-5-chlorodifluoromethyl-4-pyrazolecarboxylic acid ethyl ester (2.07 g, 7.18 mmol, 72%) was isolated as a colourless liquid.

$^1$H NMR (CDCl$_3$, 300 MHz, 25° C.): δ=6.97 (t, 1H, CHF$_2$, J$_{H-F}$=53.9 Hz,), 4.37 (q, 2H, CH$_2$, J=7.1 Hz), 4.10 (t, 3H, N—CH$_3$, J$_{H-F}$=2.2 Hz), 1.38 (t, 3H, CH$_3$, J=7.1 Hz) ppm. $^{13}$C NMR (CDCl$_3$, 75 MHz, 25° C.): δ=160.3 (CO), 145.3 (t, C$_{IV}$arom, J$_{C-F}$=25.7 Hz), 137.5 (t, C$_{IV}$arom, J$_{C-F}$=33.3 Hz), 119.9 (t, CF$_2$Cl, J$_{C-F}$=288.8 Hz), 112.7 (C$_{IV}$arom), 109.1 (t, CHF$_2$, J$_{C-F}$=237.8 Hz), 61.8 (CH$_2$), 40.6 (t, N—CH$_3$, J$_{C-F}$=4.6 Hz), 13.7 (CH$_3$) ppm. $^{19}$F NMR (CDCl$_3$, 282 MHz, 25° C.): δ=−47.9 (CF$_2$Cl), −116.7 (CHF$_2$, J$_{F-H}$=53.9 Hz) ppm.

Example 11

N-Methyl-3-difluoromethyl-5-chlorodifluoromethyl-4-pyrazolecarboxylic acid

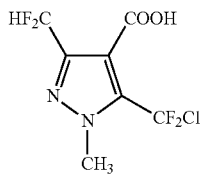

N-Methyl-3-difluoromethyl-5-chlorodifluoromethyl-4-pyrazolecarboxylic acid ethyl ester (0.5 g, 1.73 mmol) in ethanol (3 ml) was admixed gradually with an 8N aqueous sodium hydroxide solution (0.7 ml) and stirred at room temperature for 3 h. The solvent was removed by rotary evaporation; the residue was taken up in water (10 ml) and extracted with diethyl ether (10 ml). Acidification to pH 1 with 6M HCl was followed by extraction with ethyl acetate (3×10 ml). The combined organic phases were dried over sodium sulphate and filtered, and the solvent was removed by rotary evaporation. N-Methyl-3-difluoromethyl-5-chlorodifluoromethyl-4-pyrazolecarboxylic acid (0.36 g, 1.38 mmol, 80%) was isolated as a colourless solid.

$^1$H NMR (CDCl$_3$, 300 MHz, 25° C.): δ=12.15 (brs, 1H, COOH), 7.07 (t, 1H, CHF$_2$, J$_{H-F}$=53.6 Hz), 4.15 (t, 3H, N—CH$_3$, J$_{H-F}$=2.1 Hz) ppm. $^{13}$C NMR (CDCl$_3$, 75 MHz, 25° C.): δ=165.8 (CO), 146.4 (t, C$_{IV}$arom, J$_{C-F}$=25.3 Hz), 138.9 (t, C$_{IV}$arom, J$_{C-F}$=33.6 Hz), 119.6 (t, CF$_2$Cl, J$_{C-F}$=289.4 Hz), 111.15 (C$_{IV}$arom), 108.8 (t, CHF$_2$, J$_{C-F}$=238.4 Hz), 41.0 (t, N—CH$_3$, J$_{C-F}$=4.9 Hz) ppm. $^{19}$F NMR (CDCl$_3$, 282 MHz, 25° C.): δ=−48.1 (CF$_2$Cl), −117.2 (CHF$_2$, J$_{F-H}$=53.6 Hz) ppm.

Example 12

N—H-3-Difluoromethyl-5-chlorodifluoromethyl-4-pyrazolecarboxylic acid ethyl ester

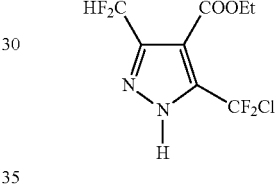

BF$_3$.OEt$_2$ (0.62 ml, 5.0 mmol) was added to a solution of TFEDMA (0.59 ml, 5.0 mmol) in dry dichloromethane (5 ml) under argon in a Teflon flask. The solution was stirred at room temperature for 15 min, before the dichloromethane was removed under reduced pressure. The residue was then taken up in dry acetonitrile (5 ml). In a second Teflon flask, ethyl 4-chloro-4,4-difluoroacetoacetate (1.0 g, 5.0 mmol) was added to a solution of pyridine (1.19 g, 15 mmol) in dry acetonitrile (10 ml) and the mixture was stirred at room temperature for 15 min. To this were added dropwise, at −30° C., the contents of the first flask. The reaction mixture was brought to room temperature in the cold bath and stirred overnight. Hydrazine hydrate (0.37 ml, 7.5 mmol) was then added dropwise at room temperature and the mixture was stirred overnight. The solvent was removed under reduced pressure and the residue was purified by flash chromatography on silica gel with a pentanes/diethyl ether mixture (9:1-7:3). N—H-3-Difluoromethyl-5-chlorodifluoromethyl-4-pyrazolecarboxylic acid ethyl ester (0.99 g, 3.61 mmol, 72%) was isolated as a pale yellowish oil.

$^1$H NMR (CDCl$_3$, 300 MHz, 25° C.): δ=11.62 (brs, 1H, NH), 7.25 (t, 2H, CHF$_2$, J$_{H-F}$=53.5 Hz), 4.41 (q, 2H, CH$_2$, J=7.1 Hz), 1.41 (t, 3H, CH$_3$, J=7.1 Hz) ppm. $^{13}$C NMR (CDCl$_3$, 75 MHz, 25° C.): δ=160.6 (CO), 146.3 (t, C$_{IV}$arom, J$_{C-F}$=32.3 Hz), 142.7 (t, CHF$_2$, J$_{C-F}$=29.3 Hz), 121.3 (t, CF$_2$Cl, J$_{C-F}$=287.3 Hz), 110.8 (C$_{IV}$arom), 109.1 (t, CHF$_2$, J$_{C-F}$=240.2 Hz), 62.0 (CH$_2$), 13.6 (CH$_3$) ppm. $^{19}$F NMR (CDCl$_3$, 282 MHz, 25° C.): δ=−49.6 (CF$_2$Cl), −116.8 (CHF$_2$, J$_{F-H}$=53.5 Hz) ppm.

Example 13

N-Methyl-3-difluoromethyl-5-pentafluoroethyl-4-pyrazolecarboxylic acid ethyl ester

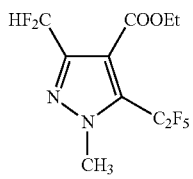

BF$_3$.OEt$_2$ (1.24 ml, 10.0 mmol) was added to a solution of TFEDMA (1.20 ml, 10.0 mmol) in dry dichloromethane (10 ml) under argon in a Teflon flask. The solution was stirred at room temperature for 15 min. before the dichloromethane was removed under reduced pressure. The residue was then taken up in dry acetonitrile (10 ml). In a second Teflon flask, ethyl 4,4,5,5,5-pentafluoroacetoacetate (1.75 ml, 10.0 mmol) was added to a solution of pyridine (2.42 ml, 30.0 mmol) in dry acetonitrile (20 ml) and the mixture was stirred at room temperature for 15 min. To this were added dropwise, at −30° C., the contents of the first flask. The reaction mixture was brought to room temperature in the cold bath and stirred overnight. Methyl hydrazine (0.79 ml, 15.0 mmol) was then added dropwise at room temperature and the mixture was stirred overnight. The solvent was removed under reduced pressure and the residue was purified by flash chromatography on silica gel with a pentanes/diethyl ether mixture (10:0-8:2). N-Methyl-3-difluoromethyl-5-pentafluoroethyl-4-pyrazolecarboxylic acid ethyl ester (2.42 g, 7.52 mmol, 75%) was isolated as a colourless liquid.

$^1$H NMR (CDCl$_3$, 300 MHz, 25° C.): δ=7.00 (t, 1H, CHF$_2$, J$_{H-F}$=53.9 Hz,), 4.35 (q, 2H, CH$_2$, J=7.1 Hz), 4.10 (t, 3H, N—CH$_3$, J$_{H-F}$=2.2 Hz), 1.35 (t, 3H, CH$_3$, J=7.1 Hz) ppm. $^{13}$C NMR (CDCl$_3$, 75 MHz, 25° C.): δ=160.2 (CO), 146.1 (t, C$_{IV}$arom, J$_{C-F}$=25.6 Hz), 131.1 (t, C$_{IV}$arom, J$_{C-F}$=29.6 Hz), 118.6 (qt, CF$_2$CF$_3$, J$^1_{C-F}$=287.1 Hz, J$^3_{C-F}$=37.7 Hz), 116.3 (C$_{IV}$arom), 109.98 (tq, CF$_2$CF$_3$, J$^1_{C-F}$=192.0 Hz, J$^3_{C-F}$=41.7 Hz), 109.1 (t, CHF$_2$, J$^1_{C-F}$=238.1 Hz), 61.9 (CH$_2$), 41.0 (t, N—CH$_3$, J$_{C-F}$=4.3 Hz), 13.8 (CH$_3$) ppm. $^{19}$F NMR (CDCl$_3$, 282 MHz, 25° C.): δ=−83.7 (CF$_2$CF$_3$), −109.5 (CF$_2$CF$_3$), −116.8 (CHF$_2$, J$_{F-H}$=53.9 Hz) ppm.

Example 14

N-Methyl-3-difluoromethyl-5-pentafluoroethyl-4-pyrazolecarboxylic acid

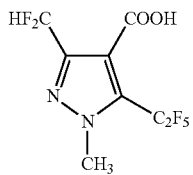

N-Methyl-3-difluoromethyl-5-pentafluoroethyl-4-pyrazolecarboxylic acid ethyl ester (0.5 g, 1.55 mmol) in ethanol (3 ml) was admixed gradually with an 8N aqueous sodium hydroxide solution (0.6 ml) and stirred at room temperature for 3 h. The solvent was removed by rotary evaporation; the residue was taken up in water (10 ml) and extracted with diethyl ether (10 ml). Acidification to pH 1 with 6M HCl was followed by extraction with ethyl acetate (3×10 ml). The combined organic phases were dried over sodium sulphate and filtered, and the solvent was removed by rotary evaporation. N-Methyl-3-difluoromethyl-5-pentafluoroethyl-4-pyrazolecarboxylic acid (0.44 g, 1.50 mmol, 97%) was isolated as a colourless solid.

$^1$H NMR (CDCl$_3$, 300 MHz, 25° C.): δ=11.16 (brs, 1H, COOH), 7.09 (t, 1H, CHF$_2$, J$_{H-F}$=53.6 Hz,), 4.15 (t, 3H, N—CH$_3$, J$_{H-F}$=2.4 Hz) ppm. $^{13}$C NMR (CDCl$_3$, 75 MHz, 25° C.): δ=165.2 (CO), 147.2 (t, C$_{IV}$arom, J$_{C-F}$=25.2 Hz), 132.5 (t, C$_{IV}$arom, J$_{C-F}$=29.8 Hz), 118.5 (qt, CF$_2$CF$_3$, J$^1_{C-F}$=287.0 Hz, J$^3_{C-F}$=37.5 Hz), 114.6 (C$_{IV}$arom), 109.9 (tq, CF$_2$CF$_3$, J$^1_{C-F}$=258.0 Hz, J$^3_{C-F}$=41.7 Hz), 108.8 (t, CHF$_2$, J$^1_{C-F}$=238.6 Hz), 41.4 (t, N—CH$_3$, J$_{C-F}$=4.8 Hz) ppm.

Example 15

N—H-3-Difluoromethyl-5-pentafluoroethyl-4-pyrazolecarboxylic acid ethyl ester

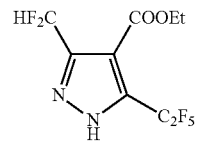

BF$_3$.OEt$_2$ (1.24 ml, 10.0 mmol) was added to a solution of TFEDMA (1.20 ml, 10.0 mmol) in dry dichloromethane (10 ml) under argon in a Teflon flask. The solution was stirred at room temperature for 15 min, before the dichloromethane was removed under reduced pressure. The residue was then taken up in dry acetonitrile (10 ml). In a second Teflon flask, ethyl 4,4,5,5,5-pentafluoroacetoacetate (1.75 ml, 10.0 mmol) was added to a solution of pyridine (2.42 ml, 30.0 mmol) in dry acetonitrile (20 ml) and the mixture was stirred at room temperature for 15 min. To this were added dropwise, at −30° C., the contents of the first flask. The reaction mixture was brought to room temperature in the cold bath and stirred overnight. Hydrazine hydrate (0.74 ml, 15.0 mmol) was then added dropwise at room temperature and the mixture was stirred overnight. The solvent was removed under reduced pressure and the residue was purified by flash chromatography on silica gel with a pentanes/diethyl ether mixture (10:0-8:2). N—H-3-Difluoromethyl-5-pentafluoroethyl-4-pyrazolecarboxylic acid ethyl ester (2.06 g, 6.70 mmol, 67%) was isolated as a colourless oil.

$^1$H NMR (CDCl$_3$, 300 MHz, 25° C.): δ=12.69 (brs, 1H, COOH), 7.26 (t, 1H, CHF$_2$, J$_{H-F}$=53.5 Hz,), 4.40 (q, 2H, CH$_2$, J=7.1 Hz), 1.39 (t, 3H, CH$_3$, J=7.1 Hz) ppm. $^{13}$C NMR (CDCl$_3$, 75 MHz, 25° C.): δ=160.6 (CO), 141.8 (t, C$_{IV}$arom, J$_{C-F}$=25.9 Hz), 141.1 (t, C$_{IV}$arom, J$_{C-F}$=31.7 Hz), 118.7 (qt, CF$_2$CF$_3$, J$^1_{C-F}$=286.6 Hz, J$^3_{C-F}$=36.3 Hz), 113.2 (C$_{IV}$arom), 110.1 (tq, CF$_2$CF$_3$, J$^1_{C-F}$=252.9 Hz, J$^3_{C-F}$=39.5 Hz), 107.5 (t, CHF$_2$, J$^1_{C-F}$=238.8 Hz), 62.0 (CH$_2$), 13.6 (CH$_3$) ppm. $^{19}$F NMR (CDCl$_3$, 282 MHz, 25° C.): δ=−83.2 (CF$_2$CF$_3$), −110.1 (CF$_2$CF$_3$), −117.2 (CHF$_2$, J$_{F-H}$=53.5 Hz) ppm.

Example 16

N-Methyl-3-difluoromethyl-5-trifluoromethyl-4-pyrazolecarboxylic acid ethyl ester

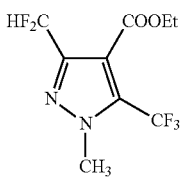

BF$_3$ (0.34 g, 5 mmol) as a 17% solution in acetonitrile (0.76 ml) was added to a solution of TFEDMA (0.59 ml, 5.0 mmol) in CH3CN (5 ml) under argon in a Teflon flask. The solution was stirred at room temperature for 15 min. In a second Teflon flask, ethyl 4,4,4-trifluoroacetoacetate (0.73 ml, 5.0 mmol) was added to a solution of potassium fluorides (0.88 g, 15.0 mmol) in dry acetonitrile (10 ml) and the mixture was stirred at room temperature for 15 min. To this were added dropwise, at −30° C. the contents of the first flask. The reaction mixture was brought to room temperature in the cold bath and stirred overnight. Methyl hydrazine (0.32 ml, 6.0 mmol) was then added dropwise at room temperature and the mixture was stirred overnight. The solvent was removed under reduced pressure and the residue was purified by flash chromatography on silica gel with a pentanes/diethyl ether mixture (9:1-8:2). N-Methyl-3-difluoromethyl-5-trifluoromethyl-4-pyrazolecarboxylic acid ethyl ester (0.95 g) was obtained as a yellow oil.

Example 17

N-Phenyl-3-difluoromethyl-5-trifluoromethyl-4-pyrazolecarboxylic acid ethyl ester

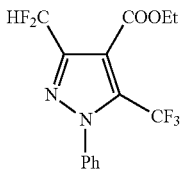

BF$_3$.OEt$_2$ (2.5 ml, 20.0 mmol) was added to a solution of TFEDMA (2.4 ml, 20.0 mmol) in dry dichloromethane (20 ml) under argon in a Teflon flask. The solution was stirred at room temperature for 15 min, before the dichloromethane was removed under reduced pressure. The residue was then taken up in dry acetonitrile (20 ml). In a second Teflon flask, ethyl 4,4,4-trifluoroacetoacetate (2.8 ml, 20.0 mmol) was added to a solution of pyridine (4.7 g, 60.0 mmol) in dry acetonitrile (40 ml) and the mixture was stirred at room temperature for 15 min. To this were added dropwise, at −30° C. the contents of the first flask. The reaction mixture was brought to room temperature in the cold bath and stirred overnight. Phenyl hydrazine (3.0 ml, 30.0 mmol) was then added dropwise at room temperature and the mixture was stirred overnight. The solvent was removed under reduced pressure and the residue was purified by flash chromatography on silica gel with a pentanes/diethyl ether mixture (9:1). N-Phenyl-3-difluoromethyl-5-trifluoromethyl-4-pyrazolecarboxylic acid ethyl ester (4.47 g, 13.4 mmol, 67%) was isolated as a colourless solid.

$^1$H NMR (CDCl$_3$, 300 MHz, 25° C.): δ=7.55-7.42 (m, 5H, N-Ph), 7.05 (t, 1H, CHF$_2$, J$_{H-F}$=53.7 Hz), 4.42 (q, 2H, CH$_2$, J=7.1 Hz), 1.40 (t, 3H, CH$_3$, J=7.1 Hz) ppm. $^{13}$C NMR (CDCl$_3$, 75 MHz, 25° C.): δ=160.3 (CO), 146.7 (t, C$_{IV}$arom, J$_{C-F}$=26.2 Hz), 138.8 (N—C$_{IV}$ phenyl), 133.8 (q, C$_{IV}$arom, J$_{C-F}$=40.1 Hz), 130.4 (CH phenyl), 129.3 (CH phenyl), 125.9 (CH phenyl), 118.6 (q, CF$_3$, J$_{C-F}$=271.9 Hz), 115.0 (C$_{IV}$arom), 109.2 (t, CHF$_2$, J$_{C-F}$=238.4 Hz), 62.0 (CH$_2$), 13.8 (CH$_3$) ppm. $^{19}$F NMR (CDCl$_3$, 282 MHz, 25° C.): δ=−56.8 (CF$_3$), −117.3 ppm.

Example 18

N-Phenyl-3-difluoromethyl-5-trifluoromethyl-4-pyrazolecarboxylic acid

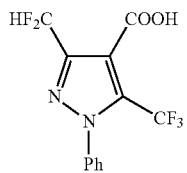

N-Phenyl-3-difluoromethyl-5-trifluoromethyl-4-pyrazolecarboxylic acid ethyl ester (3.0 g, 9.0 mmol) in ethanol (15 ml) was admixed gradually with an 8N aqueous sodium hydroxide solution (3.4 ml) and stirred at room temperature for 3 h. The solvent was removed by rotary evaporation; the residue was taken up in water (40 ml) and extracted with diethyl ether (20 ml). Acidification to pH 1 with 6M HCl was followed by extraction with ethyl acetate (3×30 ml). The combined organic phases were dried over sodium sulphate and filtered, and the solvent was removed by rotary evaporation. N-Phenyl-3-difluoromethyl-5-trifluoromethyl-4-pyrazolecarboxylic acid (2.58 g, 8.43 mmol, 94%) was isolated as a colourless solid.

$^1$H NMR (CDCl$_3$, 300 MHz, 25° C.): δ=11.53 (brs, 1H, —COOH), 7.58-7.44 (m, 5H, N-phenyl), 7.15 (t, 1H, CHF$_2$, J$_{H-F}$=53.5 Hz) ppm. $^{13}$C NMR (CDCl$_3$, 75 MHz, 25° C.): δ=165.8 (CO), 147.6 (t, C$_{IV}$arom, J$_{C-F}$=25.8 Hz), 138.7 (N—C$_{IV}$ phenyl), 135.1 (q, C$_{IV}$arom, J$_{C-F}$=40.4 Hz), 130.6 (CH phenyl), 129.4 (CH phenyl), 125.9 (CH phenyl), 118.4 (q, CF$_3$, J$_{C-F}$=272.3 Hz), 114.3 (C$_{IV}$arom), 108.9 (t, CHF$_2$, J$_{C-F}$=239.0 Hz) ppm. $^{19}$F NMR (CDCl$_3$, 282 MHz, 25° C.): δ=−56.8 (CF$_3$), −117.8 (CHF$_2$) ppm.

Example 19

N-Phenyl-3-difluoromethyl-5-chlorodifluoromethyl-4-pyrazolecarboxylic acid ethyl ester

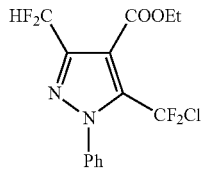

BF$_3$.OEt$_2$ (2.5 ml, 20.0 mmol) was added to a solution of TFEDMA (2.4 ml, 20.0 mmol) in dry dichloromethane (20 ml) under argon in a Teflon flask. The solution was stirred at room temperature for 15 min, before the dichloromethane was removed under reduced pressure. The residue was then taken up in dry acetonitrile (20 ml). In a second Teflon flask, ethyl 4-chloro-4,4-difluoroacetoacetate (4.0 g, 20.0 mmol) was added to a solution of pyridine (4.7 g, 60.0 mmol) in dry acetonitrile (40 ml) and the mixture was stirred at room temperature for 15 min. To this were added dropwise, at −30° C., the contents of the first flask. The reaction mixture was brought to room temperature in the cold bath and stirred overnight. Phenyl hydrazine (3.0 ml, 30.0 mmol) was then added dropwise at room temperature and the mixture was stirred overnight. The solvent was removed under reduced pressure and the residue was purified by flash chromatography on silica gel with a pentanes/diethyl ether mixture (9:1). N-Phenyl-3-difluoromethyl-5-chlorodifluoromethyl-4-pyrazolecarboxylic acid ethyl ester (3.67 g, 10.5 mmol, 53%) was isolated as a colourless solid.

$^1$H NMR (CDCl$_3$, 300 MHz, 25° C.): δ=7.55-7.45 (m, 5H, N-Ph), 7.03 (t, 1H, CHF$_2$, J$_{H-F}$=53.7 Hz), 4.42 (q, 2H, CH$_2$, J=7.1 Hz), 1.41 (t, 3H, CH$_3$, J=7.2 Hz) ppm. $^{13}$C NMR (CDCl$_3$, 75 MHz, 25° C.): δ=160.5 (CO), 146.5 (t, C$_{IV}$arom, J$_{C-F}$=26.3 Hz), 138.9 (N—C$_{IV}$ phenyl), 138.3 (t, C$_{IV}$arom, J$_{C-F}$=32.7 Hz), 130.3 (CH phenyl), 129.2 (CH phenyl), 126.2 (CH phenyl), 119.5 (t, CF$_3$, J$_{C-F}$=290.0 Hz), 115.6 (C$_{IV}$arom), 109.3 (t, CHF$_2$, J$_{C-F}$=238.4 Hz), 62.0 (CH$_2$), 13.9 (CH$_3$) ppm. $^{19}$F NMR (CDCl$_3$, 282 MHz, 25° C.): δ=−46.6 (CF$_2$Cl), −117.3 (CHF$_2$) ppm.

Example 20

N-Phenyl-3-difluoromethyl-5-chlorodifluoromethyl-4-pyrazolecarboxylic acid

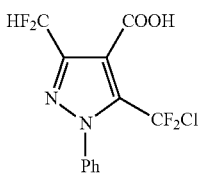

N-Phenyl-3-difluoromethyl-5-chlorodifluoromethyl-4-pyrazolecarboxylic acid ethyl ester (3.0 g, 8.56 mmol) in ethanol (15 ml) was admixed gradually with an 8N aqueous sodium hydroxide solution (3.2 ml) and stirred at room temperature for 3 h. The solvent was removed by rotary evaporation; the residue was taken up in water (40 ml) and extracted with diethyl ether (20 ml). Acidification to pH 1 with 6M HCl was followed by extraction with ethyl acetate (3×30 ml). The combined organic phases were dried over sodium sulphate and filtered, and the solvent was removed by rotary evaporation. N-Phenyl-3-difluoromethyl-5-chlorodifluoromethyl-4-pyrazolecarboxylic acid (2.74 g, 8.49 mmol, 99%) was isolated as a colourless solid.

$^1$H NMR (CDCl$_3$, 300 MHz, 25° C.): δ=7.57-7.47 (m, 5H, N-phenyl), 7.12 (t, 1H, CHF$_2$, J$_{H-F}$=53.5 Hz) ppm. $^{13}$C NMR (CDCl$_3$, 75 MHz, 25° C.): δ=165.9 (CO), 147.4 (t, C$_{IV}$arom, J$_{C-F}$=25.8 Hz), 139.8 (t, C$_{IV}$arom, J$_{C-F}$=33.0 Hz), 138.9 (N—C$_{IV}$ phenyl), 130.5 (CH phenyl), 129.3 (CH phenyl), 126.2 (CH phenyl), 119.2 (t, CF$_2$Cl, J$_{C-F}$=290.6 Hz), 112.1 (C$_{IV}$arom), 108.9 (t, CHF$_2$, J$_{C-F}$=239.0 Hz) ppm. $^{19}$F NMR (CDCl$_3$, 282 MHz, 25° C.): δ=−46.9 (CF$_2$Cl), −117.8 (CHF$_2$) ppm.

Example 21

N-Phenyl-3-difluoromethyl-5-pentafluoroethyl-4-pyrazolecarboxylic acid ethyl ester

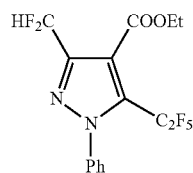

BF$_3$.OEt$_2$ (2.5 ml, 20.0 mmol) was added to a solution of TFEDMA (2.4 ml, 20.0 mmol) in dry dichloromethane (20 ml) under argon in a Teflon flask. The solution was stirred at room temperature for 15 min, before the dichloromethane was removed under reduced pressure. The residue was then taken up in dry acetonitrile (20 ml). In a second Teflon flask, ethyl 4,4,5,5,5-pentafluoroacetoacetate (3.5 ml, 11.4 mmol) was added to a solution of pyridine (2.7 g, 34.4 mmol) in dry acetonitrile (40 ml) and the mixture was stirred at room temperature for 15 min. To this were added dropwise, at −30° C., the contents of the first flask. The reaction mixture was brought to room temperature in the cold bath and stirred overnight. Phenyl hydrazine (2.0 ml, 20.0 mmol) was then added dropwise at room temperature and the mixture was stirred overnight. The solvent was removed under reduced pressure and the residue was purified by flash chromatography on silica gel with a pentanes/diethyl ether mixture (9:1). N-Phenyl-3-difluoromethyl-5-pentafluoroethyl-4-pyrazolecarboxylic acid ethyl ester (3.73 g, 9.70 mmol, 85%) was isolated as a beige solid.

$^1$H NMR (CDCl$_3$, 300 MHz, 25° C.): δ=7.58-7.35 (m, 5H, N-Ph), 7.04 (t, 1H, CHF$_2$, J$_{H-F}$=53.8 Hz), 4.40 (q, 2H, CH$_2$, J=7.1 Hz), 1.38 (t, 3H, CH$_3$, J=7.2 Hz) ppm. $^{13}$C NMR (CDCl$_3$, 75 MHz, 25° C.): δ=165.8 (CO), 147.6 (t, C$_{IV}$arom, J$_{C-F}$=25.8 Hz), 138.7 (N—C$_{IV}$ phenyl), 135.1 (q, C$_{IV}$arom, J$_{C-F}$=40.4 Hz), 130.6 (CH phenyl), 129.4 (CH phenyl), 125.9 (CH phenyl), 118.4 (qt, CF$_3$, J$^1_{C-F}$=287.5 Hz, J$^3_{C-F}$=37.5 Hz), 116.4 (C$_{IV}$arom), 109.6 (tq, CF$_2$, J$^1_{C-F}$=255.3 Hz, J$^3_{C-F}$=41.6 Hz), 109.4 (t, CHF$_2$, J$_{C-F}$=238.6 Hz), 62.1 (CH$_2$), 13.7 (CH$_3$) ppm. $^{19}$F NMR (CDCl$_3$, 282 MHz, 25° C.): δ=−83.6 (CF$_3$), −107.1 (CF$_2$), −117.3 (CHF$_2$) ppm.

Example 22

N-Phenyl-3-difluoromethyl-5-pentafluoroethyl-4-pyrazolecarboxylic acid

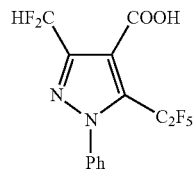

N-Phenyl-3-difluoromethyl-5-pentafluoroethyl-4-pyrazolecarboxylic acid ethyl ester (3.0 g, 7.81 mmol) in ethanol (15 ml) was admixed gradually with an 8N aqueous sodium hydroxide solution (3.0 ml) and stirred at room temperature for 3 h. The solvent was removed by rotary evaporation, the residue was taken up in water (40 ml) and extracted with diethyl ether (20 ml). Acidification to pH 1 with 6M HCl was followed by extraction with ethyl acetate (3×30 ml). The combined organic phases were dried over sodium sulphate and filtered, and the solvent was removed by rotary evaporation. N-Phenyl-3-difluoromethyl-5-pentafluoroethyl-4-pyrazolecarboxylic acid (2.71 g, 7.61 mmol, 98%) was isolated as a colourless solid.

$^1$H NMR (CDCl$_3$, 300 MHz, 25° C.): δ=7.60-7.37 (m, 5H, N-phenyl), 7.14 (t, 1H, CHF$_2$, J$_{H-F}$=53.6 Hz) ppm. $^{13}$C NMR (MeOD, 75 MHz, 25° C.): δ=164.0 (CO), 148.6 (t, C$_{IV}$arom, J$_{C-F}$=25.6 Hz), 141.4 (N—C$_{IV}$ phenyl), 133.4 (CH phenyl), 133.1 (t, C$_{IV}$arom, J$_{C-F}$=29.1 Hz), 131.7 (CH phenyl), 130.0 (CH phenyl), 120.6 (qt, CF$_3$, J$^1_{C-F}$=287.6 Hz, J$^3_{C-F}$=37.9 Hz), 120.1 (C$_{IV}$arom), 112.3 (t, CHF$_2$, J$_{C-F}$=236.4 Hz), 112.1 (tq, CF$_2$, J$^1_{C-F}$=262.5 Hz, J$^3_{C-F}$=40.5 Hz) ppm. $^{19}$F NMR (CDCl$_3$, 282 MHz, 25° C.): δ=−83.5 (CF$_3$), −107.1 (CF$_2$), −117.9 (CHF$_2$) ppm.

Example 23

N-tert-Butyl-3-difluoromethyl-5-trifluoromethyl-4-pyrazolecarboxylic acid ethyl ester

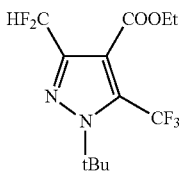

BF$_3$.OEt$_2$ (2.7 ml, 22.0 mmol) was added to a solution of TFEDMA (2.5 ml, 22.0 mmol) in dry dichloromethane (20 ml) under argon in a Teflon flask. The solution was stirred at room temperature for 15 min, before the dichloromethane was removed under reduced pressure. The residue was then taken up in dry acetonitrile (20 ml). In a second Teflon flask, ethyl 4,4,4-trifluoroacetoacetate (2.8 ml, 20.0 mmol) was added to a solution of pyridine (7.1 g, 90.0 mmol) in dry acetonitrile (40 ml) and the mixture was stirred at room temperature for 15 min. To this were added dropwise, at −30° C. the contents of the first flask. The reaction mixture was brought to room temperature in the cold bath and stirred overnight. tert-Butyl hydrazine hydrochloride (3.74 g, 30.0 mmol) was added to a solution of potassium hydroxide (1.68 g, 30 mmol) in methanol (10 ml) and the mixture was stirred at room temperature for 30 minutes. This mixture was then added to the previously prepared intermediate (ethyl 2-(2,2,2-trifluoroacetyl)-3-(dimethylamino)-4,4-difluorobut-2-enoate) and the mixture was stirred overnight. The solvent was removed under reduced pressure and the residue was purified by flash chromatography on silica gel with a pentanes/diethyl ether mixture (9:1). N-tert-Butyl-3-difluoromethyl-5-trifluoromethyl-4-pyrazolecarboxylic acid ethyl ester (3.29 g, 10.5 mmol, 53%) was isolated as a yellow oil.

$^1$H NMR (CDCl$_3$, 300 MHz, 25° C.): δ=6.80 (t, 1H, CHF$_2$, J$_{H-F}$=54.0 Hz), 4.37 (q, 2H, CH$_2$, J=7.1 Hz), 1.70 (s, 9H, tBu), 1.36 (t, 3H, CH$_3$, J=7.1 Hz) ppm. $^{13}$C NMR (CDCl$_3$, 75 MHz, 25° C.): δ=161.5 (CO), 141.9 (t, C$_{IV}$arom, J$_{C-F}$=27.8 Hz), 131.5 (q, C$_{IV}$arom, J$_{C-F}$=40.6 Hz), 119.3 (q, CF$_3$, J$_{C-F}$=270.7 Hz), 116.9 (C$_{IV}$arom), 109.9 (t, CHF$_2$, J$_{C-F}$=236.7 Hz), 66.0 (N—C$_{IV}$ tBu), 62.0 (CH$_2$), 29.9 (q, CH$_3$ tBu, J$_{C-F}$=2.4 Hz), 13.8 (CH$_3$) ppm. $^{19}$F NMR (CDCl$_3$, 282 MHz, 25° C.): δ=−53.3 (CF$_3$), −114.4 (CHF$_2$, J$_{F-H}$=54.0 Hz) ppm.

Example 24

N-tert-Butyl-3-difluoromethyl-1-trifluoromethyl-4-pyrazolecarboxylic acid

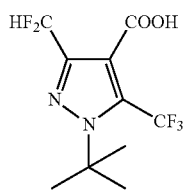

N-tert-Butyl-3-difluoromethyl-5-trifluoromethyl-4-pyrazolecarboxylic acid ethyl ester (2.48 g, 7.9 mmol) in ethanol (15 ml) was admixed gradually with an 8N aqueous sodium hydroxide solution (3.0 ml) and stirred at room temperature for 3 h. The solvent was removed by rotary evaporation; the residue was taken up in water (40 ml) and extracted with diethyl ether (20 ml). Acidification to pH 1 with 6M HCl was followed by extraction with ethyl acetate (3×30 ml). The combined organic phases were dried over sodium sulphate and filtered, and the solvent was removed by rotary evaporation. N-tert-Butyl-3-difluoromethyl-5-trifluoromethyl-4-pyrazolecarboxylic acid (2.15 g, 7.52 mmol, 94%) was isolated as a yellow solid.

$^1$H NMR (CDCl$_3$, 300 MHz, 25° C.): δ=6.92 (t, 1H, CHF$_2$, J$_{H-F}$=53.8 Hz), 1.74 (s, 9H, tBu) ppm. $^{13}$C NMR (CDCl$_3$, 75 MHz, 25° C.): δ=166.8 (CO), 142.9 (t, C$_{IV}$arom, J$_{C-F}$=26.9 Hz), 132.9 (q, C$_{IV}$arom, J$_{C-F}$=41.1 Hz), 119.1 (q, CF$_3$, J$_{C-F}$=271.1 Hz), 115.1 (C$_{IV}$arom), 109.5 (t, CHF$_2$, J$_{C-F}$=237.5 Hz), 66.7 (N—C$_{IV}$ tBu), 29.9 (q, CH$_3$ tBu, J$_{C-F}$=2.5 Hz) ppm. $^{19}$F NMR (CDCl$_3$, 282 MHz, 25° C.): δ=−54.0 (CF$_3$), −116.0 (CHF$_2$) ppm.

Example 25

N-tert-Butyl-3-difluoromethyl-5-pentafluoroethyl-4-pyrazolecarboxylic acid ethyl ester

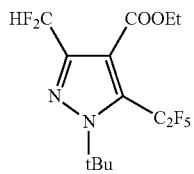

BF$_3$.OEt$_2$ (2.7 ml, 22.0 mmol) was added to a solution of TFEDMA (2.5 ml, 22.0 mmol) in dry dichloromethane (20 ml) under argon in a Teflon flask. The solution was stirred at room temperature for 15 min, before the dichloromethane was removed under reduced pressure. The residue was then taken up in dry acetonitrile (20 ml). In a second Teflon flask, ethyl 4,4,5,5,5-pentafluoroacetoacetate (4.68 g, 20.0 mmol)

was added to a solution of pyridine (7.1 g, 90.0 mmol) in dry acetonitrile (40 ml) and the mixture was stirred at room temperature for 15 min. To this were added dropwise, at −30° C., the contents of the first flask. The reaction mixture was brought to room temperature in the cold bath and stirred overnight. tert-Butyl hydrazine hydrochloride (3.74 g, 30.0 mmol) was then added dropwise at room temperature and the mixture was stirred overnight. The solvent was removed under reduced pressure and the residue was purified by flash chromatography on silica gel with a pentanes/diethyl ether mixture (9:1). N-tert-Butyl-3-difluoromethyl-5-pentafluoroethyl-4-pyrazolecarboxylic acid ethyl ester (2.41 g, 6.61 mmol, 33%) was isolated as a colourless oil.

$^1$H NMR (CDCl$_3$, 300 MHz, 25° C.): δ=6.83 (t, 1H, CHF$_2$, J$_{H-F}$=54.1 Hz), 4.35 (q, 2H, CH$_2$, J=7.1 Hz), 1.69 (s, 9H, tBu), 1.34 (t, 3H, CH$_3$, J=7.2 Hz) ppm. $^{13}$C NMR (CDCl$_3$, 75 MHz, 25° C.): δ=161.2 (CO), 142.8 (t, C$_{IV}$arom, J$_{C-F}$=27.3 Hz), 130.0 (q, C$_{IV}$arom, J$_{C-F}$=31.0 Hz), 118.6 (qt, CF$_3$, J$^1_{C-F}$=287.8 Hz, J$^3_{C-F}$=38.3 Hz), 118.5 (C$_{IV}$arom), 110.8 (tq, CF$_2$, J$^1_{C-F}$=258.1 Hz, J$^3_{C-F}$=41.0 Hz), 110.0 (t, CHF$_2$, J$_{C-F}$=237.2 Hz), 67.6 (N—C$_{IV}$ tBu), 62.0 (CH$_2$), 30.5 (t, CH$_3$ tBu, J$_{C-F}$=3.6 Hz), 13.7 (CH$_3$) ppm. $^{19}$F NMR (CDCl$_3$, 282 MHz, 25° C.): δ=−80.7 (CF$_3$), −100.8 (CF$_2$), −115.5 (CHF$_2$, J$_{F-H}$=54.1 Hz) ppm.

Example 26

N-tert-Butyl-3-difluoromethyl-5-pentafluoroethyl-4-pyrazolecarboxylic acid

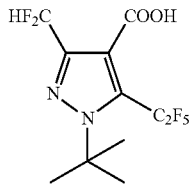

N-tert-Butyl-3-difluoromethyl-5-pentafluoroethyl-4-pyrazolecarboxylic acid ethyl ester (2.0 g, 5.50 mmol) in ethanol (10 ml) was admixed gradually with an 8N aqueous sodium hydroxide solution (2.0 ml) and stirred at room temperature for 3 h. The solvent was removed by rotary evaporation; the residue was taken up in water (40 ml) and extracted with diethyl ether (20 ml). Acidification to pH 1 with 6M HCl was followed by extraction with ethyl acetate (3×30 ml). The combined organic phases were dried over sodium sulphate and filtered, and the solvent was removed by rotary evaporation. N-tert-Butyl-3-difluoromethyl-5-pentafluoroethyl-4-pyrazolecarboxylic acid (1.83 g, 5.44 mmol, 99%) was isolated as a yellow solid.

$^1$H NMR (CDCl$_3$, 300 MHz, 25° C.): δ=11.4 (brs, 1H, COOH), 7.01 (t, 1H, CHF$_2$, J$_H$=53.9 Hz), 1.78 (s, 9H, tBu) ppm. $^{13}$C NMR (CDCl$_3$, 75 MHz, 25° C.): δ=166.5 (CO), 143.9 (t, C$_{IV}$arom, J$_{C-F}$=26.3 Hz), 131.5 (q, C$_{IV}$arom, J$_{C-F}$=31.0 Hz), 120.0 (qt, CF$_3$, J$^1_{C-F}$=288.1 Hz, J$^3_{C-F}$=38.1 Hz), 117.4 (C$_{IV}$arom), 110.6 (tq, CF$_2$, J$^1_{C-F}$=258.7 Hz, J$^3_{C-F}$=41.2 Hz), 109.5 (t, CHF$_2$, J$_{C-F}$=237.9 Hz), 68.3 (N—C$_{IV}$ tBu), 30.6 (t, CH$_3$ tBu, J$_{C-F}$=3.7 Hz) ppm. $^{19}$F NMR (CDCl$_3$, 282 MHz, 25° C.): δ=−80.3 (CF$_3$), −100.4 (CF$_2$), −116.3 (CHF$_2$, J$_{F-H}$=53.9 Hz) ppm.

Example 27

N-tert-Butyl-3,5-bis(difluoromethyl)-4-pyrazolecarboxylic acid ethyl ester

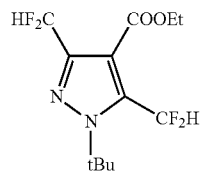

BF$_3$.OEt$_2$ (2.7 ml, 22.0 mmol) was added to a solution of TFEDMA (2.5 ml, 22.0 mmol) in dry dichloromethane (20 ml) under argon in a Teflon flask. The solution was stirred at room temperature for 15 min, before the dichloromethane was removed under reduced pressure. The residue was then taken up in dry acetonitrile (20 ml). In a second Teflon flask, ethyl 4,4-difluoroacetoacetate (2.8 ml, 20.0 mmol) was added to a solution of pyridine (7.1 g, 90.0 mmol) in dry acetonitrile (40 ml) and the mixture was stirred at room temperature for 15 min. To this were added dropwise, at −30° C., the contents of the first flask. The reaction mixture was brought to room temperature in the cold bath and stirred overnight. tert-Butyl hydrazine hydrochloride (3.74 g, 30.0 mmol) was then added to a solution of potassium hydroxide (1.68 g, 30 mmol) in methanol (10 ml) and the mixture was stirred at room temperature for 30 minutes. This mixture was then added to the previously prepared intermediate (ethyl 2-(2,2-difluoroacetyl)-3-(dimethylamino)-4,4-difluorobut-2-enoate) and the mixture was stirred overnight. The solvent was removed under reduced pressure and the residue was purified by flash chromatography on silica gel with a pentanes/diethyl ether mixture (9:1). N-tert-Butyl-3,5-di(difluoromethyl)-4-pyrazolecarboxylic acid ethyl ester (1.77 g, 5.98 mmol, 30%) was isolated as an orange oil.

$^1$H NMR (CDCl$_3$, 300 MHz, 25° C.): δ=7.71 (t, 1H, CHF$_2$, J$_{H-F}$=52.9 Hz), 6.97 (t, 1H, CHF$_2$, J$_{C-F}$=54.0 Hz), 4.37 (q, 2H, CH$_2$, J=7.1 Hz), 1.71 (s, 9H, tBu), 1.39 (t, 3H, CH$_3$, J=7.1 Hz) ppm. $^{13}$C NMR (CDCl$_3$, 75 MHz, 25° C.): δ=161.9 (CO), 143.4 (t, C$_{IV}$arom, J$_{C-F}$=25.5 Hz), 137.9 (t, C$_{IV}$arom, J$_{C-F}$=24.8 Hz), 114.5 (C$_{IV}$arom), 109.9 (t, CHF$_2$, J$_{C-F}$=237.3 Hz), 106.8 (t, CHF$_2$, J$_{C-F}$=238.3 Hz), 65.3 (N—C$_{IV}$ tBu), 61.5 (CH$_2$), 30.0 (t, CH$_3$ tBu, J$_{C-F}$=3.4 Hz), 14.0 (CH$_3$) ppm. $^{19}$F NMR (CDCl$_3$, 282 MHz, 25° C.): δ=−111.5 (CHF$_2$), −116.0 (CHF$_2$) ppm.

Example 28

N-tert-Butyl-3,5-bis(difluoromethyl)-4-pyrazolecarboxylic acid

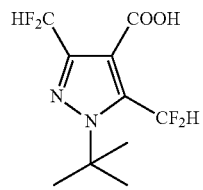

N-tert-Butyl-3,5-di(difluoromethyl)-4-pyrazolecarboxylic acid ethyl ester (3.40 g, 11.5 mmol) in ethanol (23 ml)

was admixed gradually with an 8N aqueous sodium hydroxide solution (4.3 ml) and stirred at room temperature for 3 h. The solvent was removed by rotary evaporation; the residue was taken up in water (40 ml) and extracted with diethyl ether (20 ml). Acidification to pH 1 with 6M HCl was followed by extraction with ethyl acetate (3×30 ml). The combined organic phases were dried over sodium sulphate and filtered, and the solvent was removed by rotary evaporation. N-tert-Butyl-3,5-di(difluoromethyl)-4-pyrazolecarboxylic acid (3.0 g, 11.2 mmol, 97%) was isolated as a pale reddish solid.

$^1$H NMR (CDCl$_3$, 300 MHz, 25° C.): δ=7.72 (t, 1H, CHF$_2$, $J_{H-F}$=52.7 Hz), 7.06 (t, 1H, CHF$_2$, $J_{H-F}$=53.7 Hz), 1.75 (s, 9H, tBu) ppm. $^{13}$C NMR (CDCl$_3$, 75 MHz, 25° C.): δ=167.25 (CO), 144.5 (t, $C_{IV}$arom, $J_{C-F}$=25.3 Hz), 138.8 (q, $C_{IV}$arom, $J_{C-F}$=25.1 Hz), 113.0 ($C_{IV}$arom), 109.4 (t, CF$_2$H, $J_{C-F}$=237.7 Hz), 106.5 (t, CHF$_2$, $J_{C-F}$=238.8 Hz), 65.9 (N—$C_{IV}$ tBu), 30.0 (t, CH$_3$ tBu, $J_{C-F}$=3.5 Hz) ppm. $^{19}$F NMR (CDCl$_3$, 282 MHz, 25° C.): δ=−112.5 (CHF$_2$), −117.4 (CHF$_2$) ppm.

The invention claimed is:

1. A 3,5-Bis(fluoroalkyl)pyrazole of formula (Ia) or (Ib)

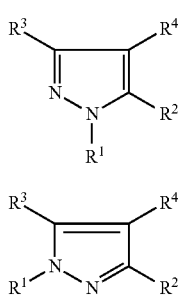

in which
R$^1$ is selected from H, C$_{1-12}$-alkyl, C$_{3-8}$-cycloalkyl, C$_{6-18}$-aryl, C$_{7-19}$-arylalkyl, C$_{7-19}$-alkylaryl, CH$_2$CN, CH$_2$CX$_3$, CH$_2$COOH, or CH$_2$COO—(C$_{1-12}$)-alkyl;
X is independently F, Cl, Br, or I;
R$^2$ is difluoromethyl
and R$^3$ is selected from C$_1$-C$_6$-haloalkyl groups,
R$^4$ is selected from the group of COOH, (C=O)OR$^5$, CN or (C=O)NR$^5$R$^6$, where R$^5$ and R$^6$ are each independently selected from the group consisting of C$_{1-12}$-alkyl, C$_{3-8}$-cycloalkyl, C$_{6-18}$-aryl, C$_{7-19}$-arylalkyl and C$_{7-19}$-alkylaryl, or where R$^5$ and R$^6$ together with the nitrogen atom to which they are bonded may form a five- or six-membered ring.

2. The compound of formula (Ia) or (Ib) according to claim 1,
wherein
R$^1$ is selected from H, methyl, CH$_2$COOH, CH$_2$COOR$^5$, CH$_2$CN, or CH$_2$CX$_3$;
X is independently F or Cl;
R$^3$ is selected from difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro,2-difluoroethyl, 2,2-dichloro-2-fluoroethyl, 2,2,2-trichloroethyl, pentafluoroethyl or 1,1,1-trifluoroprop-2-yl;
R$^4$ is selected from the group consisting of COOCH$_3$, COOEt, COOC$_3$H$_7$, CN, CONMe$_2$, and CONEt$_2$.

3. The compound of formula (Ia) or (Ib) according to claim 1, wherein
R$^1$ is selected from H, CH$_2$COOH, CH$_2$COOMe, or CH$_2$CN,
R$^3$ is selected from the group consisting of trifluoromethyl, difluoromethyl, difluorochloromethyl, and pentafluoroethyl;
R$^4$ is COOH.

4. The compound of formula (Ia) or (Ib) according to claim 1, wherein R$^1$=H; R$^2$=CF$_2$H and R$^4$=COOH.

5. The compound of formula (Ia) or (Ib) according to claim 1, wherein R$^1$=tert-butyl, R$^3$=CF$_2$H and R$^4$=CO$_2$Et or COOH.

6. The compound of formula (Ia) or (Ib) according to claim 1, wherein R$^1$=H or tert-butyl, R$^3$=CF$_3$ and R$^4$=CO$_2$Et or COOH.

7. A 3,5-Bis(fluoroalkyl)pyrazole of formula (Ia) or (Ib)

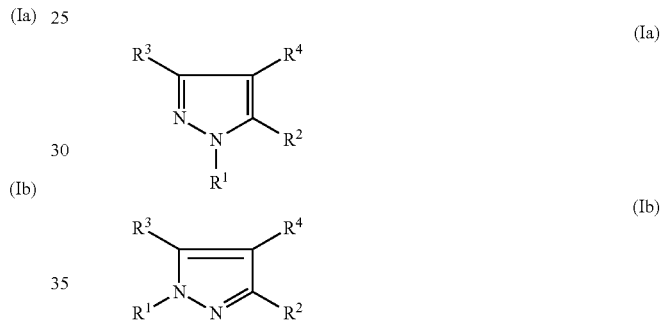

in which
R$^1$ is selected from H, C$_{1-12}$-alkyl, C$_{3-8}$-cycloalkyl, C$_{6-18}$-aryl, C$_{7-19}$-arylalkyl, C$_{7-19}$-alkylaryl, CH$_2$CN, or CH$_2$CX$_3$;
X is independently F, Cl, Br, or I;
R$^2$ is difluoromethyl
and R$^3$ is selected from C$_1$-C$_6$-haloalkyl groups,
R$^4$ is selected from the group of COOH, (C=O)OR$^5$, CN or (C=O)NR$^5$R$^6$, where R$^5$ and R$^6$ are each independently selected from the group consisting of C$_{1-12}$-alkyl, C$_{3-8}$-cycloalkyl, C$_{6-18}$-aryl, C$_{7-19}$-arylalkyl and C$_{7-19}$-alkylaryl, or where R$^5$ and R$^6$ together with the nitrogen atom to which they are bonded may form a five- or six-membered ring.

8. The compound of formula (Ia) or (Ib) according to claim 7, wherein R$^4$ is (C=O)OR$^5$.

9. The compound of formula (Ia) or (Ib) according to claim 7, wherein R$^4$ is COOH.

10. The compound of formula (Ia) or (Ib) according to claim 7, wherein R$^4$ is CN.

11. The compound of formula (Ia) or (Ib) according to claim 7, wherein R$^4$ is (C=O)NR$^5$R$^6$.

* * * * *